United States Patent [19]
Goldstein

[11] Patent Number: 5,632,778
[45] Date of Patent: May 27, 1997

[54] TREATED TISSUE FOR IMPLANTATION AND METHODS OF PREPARATION

[75] Inventor: Steven Goldstein, Atlanta, Ga.

[73] Assignee: Cryolife, Inc., Marietta, Ga.

[21] Appl. No.: 463,643

[22] Filed: Jun. 5, 1995

Related U.S. Application Data

[62] Division of Ser. No. 213,754, Mar. 14, 1994.
[51] Int. Cl.$^6$ ........................................................ A61F 2/02
[52] U.S. Cl. ............................... 623/11; 623/66; 128/898; 435/1.3; 435/378; 435/401; 435/402
[58] Field of Search ...................... 623/11, 66; 128/898; 435/240.241, 240.243; 8/94.11, 94.18

[56] References Cited

U.S. PATENT DOCUMENTS

| | | |
|---|---|---|
| 3,966,401 | 6/1976 | Hancock et al. . |
| 4,083,066 | 4/1978 | Schmitz et al. ........................ 8/94.11 |
| 4,240,794 | 12/1980 | Holman et al. . |
| 4,323,358 | 4/1982 | Lentz et al. . |
| 4,378,224 | 3/1983 | Nimni et al. . |
| 4,383,832 | 5/1983 | Fraefel et al. . |
| 4,402,697 | 9/1983 | Pollock et al. . |
| 4,405,327 | 9/1983 | Pollock . |
| 4,407,787 | 10/1983 | Stemberger . |
| 4,485,096 | 11/1984 | Bell . |
| 4,539,716 | 9/1985 | Bell . |
| 4,546,500 | 10/1985 | Bell . |
| 4,553,974 | 11/1985 | Dewanjee . |

(List continued on next page.)

FOREIGN PATENT DOCUMENTS

| | | |
|---|---|---|
| 0128706 | 12/1984 | European Pat. Off. . |
| 0267026 | 11/1987 | European Pat. Off. . |
| 0296475 | 12/1988 | European Pat. Off. . |
| 0361957 | 4/1990 | European Pat. Off. . |
| 1522286 | 2/1967 | France . |
| 2104349 | 8/1971 | France . |
| 2589165 | 4/1987 | France . |
| 2136533 | 9/1984 | United Kingdom . |
| WO83/03335 | 10/1983 | WIPO . |
| WO84/01879 | 5/1984 | WIPO . |
| WO86/02273 | 4/1986 | WIPO . |
| WO88/02263 | 4/1988 | WIPO . |
| WO89/00198 | 1/1989 | WIPO . |
| WO89/01286 | 2/1989 | WIPO . |
| WO89/08117 | 9/1989 | WIPO . |
| WO91/16009 | 10/1991 | WIPO . |
| WO91/18505 | 12/1991 | WIPO . |

OTHER PUBLICATIONS

O'Brien, et al. *A Comparison of Aortic Valve Replacement with Viable Cryopreserved and Fresh Allograft Valves, with a Note on Chromosomal Studies*, J. Thoracic & Cardiovascular Surg. 94:812–823 (1987).

Slavkin, et al., *Concepts of Epithelial–Mesenchymal Interactions During Development: Tooth and Lung Organogenesis*, J. Cellular Bioch. 26:117–125 (1984).

(List continued on next page.)

*Primary Examiner*—Paul B. Prebilic
*Attorney, Agent, or Firm*—Kenyon & Kenyon

[57] ABSTRACT

This disclosure includes a method for generating a functional hybrid bioprosthesis. Tissue formed naturally of interstitial collagens is treated to kill native cells and remove potentially immunologically active soluble molecules. Then it may be treated sequentially with extracellular matrix adhesion factor, extracellular matrix glycosaminoglycan, and growth factor appropriate to the cell type required to function within the matrix, and incubating the transplant tissue matrix with cells that are either allogeneic or autologous for the recipient thereby imparting to the matrix the characteristics of the cell type and tissue selected. Tissues with a variety of functional bioactivities can thus be formed in vitro prior to graft transplantation or implantation which will exhibit reduced or no stimulation of an immunological response in the recipient.

15 Claims, 14 Drawing Sheets

U.S. PATENT DOCUMENTS

| | | |
|---|---|---|
| 4,559,298 | 12/1985 | Fahy . |
| 4,567,847 | 2/1986 | Linner . |
| 4,609,551 | 9/1986 | Caplan . |
| 4,642,120 | 2/1987 | Nevo et al. . |
| 4,647,283 | 3/1987 | Carpentier et al. . |
| 4,648,881 | 3/1987 | Carpentier et al. . |
| 4,688,387 | 8/1987 | Conaway . |
| 4,707,998 | 11/1987 | Linner et al. . |
| 4,776,853 | 10/1988 | Klement et al. . |
| 4,785,079 | 11/1988 | Gospodarowicz . |
| 4,798,611 | 1/1989 | Freeman, Jr. . |
| 4,799,361 | 1/1989 | Linner . |
| 4,801,299 | 1/1989 | Brendel et al. . |
| 4,828,563 | 5/1989 | Muller-Lierheim . |
| 4,835,102 | 5/1989 | Bell et al. . |
| 4,838,888 | 6/1989 | Nashef . |
| 4,865,871 | 9/1989 | Livesey et al. . |
| 4,870,160 | 9/1989 | Charonis et al. . |
| 4,878,913 | 11/1989 | Aebischer et al. . |
| 4,890,457 | 1/1990 | McNally et al. . |
| 4,902,782 | 2/1990 | Gospodarowicz . |
| 4,911,710 | 3/1990 | Milthorpe et al. . |
| 4,950,483 | 8/1990 | Ksander et al. . |
| 4,960,424 | 10/1990 | Grooters . |
| 4,964,280 | 10/1990 | Piunno et al. . |
| 4,973,493 | 11/1990 | Guire . |
| 5,002,566 | 3/1991 | Carpentier et al. . |
| 5,131,850 | 7/1992 | Brockbank . |
| 5,145,770 | 9/1992 | Tubo et al. . |
| 5,192,312 | 3/1993 | Orton . |
| 5,197,985 | 3/1993 | Caplan et al. . |
| 5,215,541 | 6/1993 | Nashef et al. . |
| 5,336,616 | 8/1994 | Livesey et al. . |
| 5,512,474 | 4/1996 | Clapper et al. ............... 435/240.243 |

OTHER PUBLICATIONS

Manu–Tawiah and Martin, *Peat Extract as a Carbon Source for the Growth of Pleurotus ostreatus Mycelium*, J. Sci. Food Agric. 47:243–247 (1989).

Nichols, et al., *Cytogenetic Evaluation of Human Endothelial Cell Cultures*, C. Cellular Phys. 132:453–462 (1987).

Nanchahal, et al., *Cultured Composite Skin Grafts: Biological Skin Equivalents Permitting Massive Expansion*, The Lancet 2 (1989) 22:191–193 (Jul. 22, 1989).

Shiogama, et al., *An Improved Cryopreservation Procedure for Human Fetal Pancreas Tissues*, Biological Abstracts, vol. 85, Abstract No. 46563 (1988).

Shingh, et al., *Binding of Tumor–Derived Angiogenic Factor to High Affinity Receptor on Endothelial Cells*, J. Cell Biology 103:299a, Abstract No. 1107 (1986).

Bell, et al., *Living Tissue Formed in vitro and Accepted as Skin–Equivalent Tissue of Full Thickness*, Science 211:1052–1054 (1981).

Weinberg and Bell, *A Blood Vessel Model Constructed from Collagen and Cultured Vascular Cells*, Science 231:397–400 (1986).

Kent, et al., *Species Variation and the Success of Endothelial Seeding*, J. Vascular Surg. 9:271–276 (1989).

Hoch, et al., *In Vitro Endothelialization of an Aldehyde–Stabilized Native Vessel*, J. Surg. Res. 44:545–554 (1988).

Noyes, *Culture of Human Fetal Liver*, Proc. Soc. Exp. Biol. Med. 144:245–248 (1973).

Leapman, et al., *Transplantation of Fetal Intestine: Survival and Function in a Subcutaneous Location in Adult Animals*, Ann. Surg. 179:109–114 (1974).

Brockbank, *Repopulation of Xenograft Heart Valves with Fibroblasts*, Small Business Innovation Research Grant Application No. PHS 90–2 (submitted Aug. 15, 1990).

Ninnemann, et al., *Clinical Skin Banking: A Simplified System for Processing, Storage, and Retrieval of Human Allografts*, Third Denver Postgraduate Institute in Emergency Medicine, Denver General Hospital, Denver, Colorado, 723–725, (held Oct. 23–28, (1978).

Abbott, et al., *Absence of Antigenicity in Freeze–Dried Skin Allografts*, Cyobiology, vol. 6, No. 5, 416–418 (1970).

Athreya, et al., *Differential Susceptibility of Epithelial Cells and Fibroblasts of Human Skin to Freeze Injury*, Cryobiology, vol. 5, No. 4, 262–269 (1968).

Barlyn, et al., *Frozen Skin Autografts Protected by Dimethyl Sulfoxide*, Surgical Forum on Plastic Surgery, vol. XV, 475–477 (Oct. 1964).

Berggren, et al., *Clinical Use of Viable Frozen Human Skin*, JAMA vol. 194, No. 2, 129–131 (Oct. 1965).

Bondoc, et al., *Clinical Experience with Viable Frozen Human Skin and a Frozen Skin Bank*, Presented at Annual Meeting of American Surgical Association, Boca Raton, Florida (Mar. 24–26, 1971).

Brown, et al., *Laboratory Investigations of Skin Viability Following Preservation by Various Methods*, Surgical Forum on Plastic Surgery, vol. VI, 577–581 (Nov. 1955).

Chambler, et al., *The Use of Etox Lyophilised Skin in Burns*, Journal Plastic Surgery 22(3) 210–215 (Jul. 1969).

Chalmers, *Transplantation Immunity in Bone Homografting*, Journal of Bone and Joint Surgery, vol. 41B, No. 1, 160–179 (Feb. 1959).

Cinamon, et al., *A Simplified Testing System to Evaluate Performance After Transplantation of Human Skin Preserved in Glycerol or in Liquid Nitrogen*, Journal of Burn Care & Rehabilitation, 435–439, (Jul./Aug. 1993).

Cochrane, et al., *The Low Temperature Storage of Skin: A Preliminary Report*, Journal Plastic Surgery, vol. 21 (1968).

Cram, et al., *Short–term Preservation of Human Autografts*, presented at Annual Meeting of American Burn Association, New Orleans, LA (Mar. 1983).

De Loecker, et al., *Metabolic Changes in Human Skin Preserved at –3 and at –196C*, Cryobiology 17, 46–53 (1980).

De Loecker, et al., *Metabolic Changes in Rat Skin during Preservation and Storage in Glycerol Buffer at –196C*, Cryobiology 12, 24–30 (1976).

Dogo, *Treatment of Extensively Burned Patients with Freeze–Dried Homologous Skin (a long term appraisal of the results)*, ACTA Chirgugiae Plasticae, 187–198 (1965).

Friedlaender, et al., *Studies on the Antigenicity of Bone*, Journal Bone Joint Surgery (AM), 851–858 (Sep. 1976).

Georgiade et al., *A Clinical and Experimental Investigation of the Preservation of Skin*, Plastic & Reconstructive Surgern vol. 17, No. 1, 267–275 (Apr. 1956).

Goldman, et al., *Lyophilized Veins as Arterial Interposition Allografts*, Cryobiology 18, 306–312 (1981).

Graham, et al., *Versatility of Skin Allografts: Desirability of A Viable Frozen Tissue Bank*, The Journal of Trauma, vol. 11, 494–501 (Jun. 1971).

Gresham, *Freeze–Drying of Human Tissue for Clinical Use*, Cryobiology, vol. 1 No. 2 (1964).

Hayes, *Skin Homografts–A Life–Saving Measure in Severely Burned Children*, 22 Annual Session of American Association for Surgery of Trauma, Homestead, Hot Springs, VA (Oct. 1962).

Helenius, et al., *Solubilization of Membranes by Detergents*, Biochimica et Biophysica Acta, 415, 29–79 (1975).

Heiple, et al., *A Comparative Study of the Healing Process Following Different Types of Bone Transplantation*, Journal of Bone and Joint Surgery, vol. 45A No. 8, 1593–1616 (1963).

Hyatt, et al., *New Methods for Preserving Bone, Skin and Blood Vessels*, Postgraduate Medicine, vol. 12 No. 3 (Sep. 1952).

Kearney, et al., *Cryopreservation of Skin Using a Murine Model: Validation of a Prognostic Viability Assay*, Cryobiology 27, 24–30 (1990).

Konstantinow, et al., *Skin Banking: A Simple Method for Cryopreservation of Split–Thickness Skin and Cultured Human Epidermal Keratinocytes*, Annals of Plastic Surgery vol. 26 No. 1 (Jan. 1991).

Lichtenberg, et al., *Solubilization of Phospholipids By Detergents Structural and Kinetic Aspects*, Biochimica et Biophysica Acta 737, 285–304 (1983).

Marrangoni, *An Experimental Study on Refrigerated Skin Grafts Stored in Ten Per Cent Homologous Serum*, Plastic & Reconstructive Surgery, vol. 6 No. 6 (Dec. 1950).

McGregor, et al., *The Behaviour of Cialit–Stored and Freeze–Dried Human Fascia Lata in Rats*, Journal of Plastic Surgery 155–164 (1974).

Nathan, et al., *Burn Wounds: Selection and Preservation of Skin, Natural Products, Blood, and Blood Products for Burn Therapy*, CRC Critical Reviews in Clinical Laboratory Sciences 1–31 (May 1976).

Prows, et al., *Evaluation of Storage Conditions for Refrigerated Rabbit Skin*, Cryobiology 17, 125–129 (1980).

Raju, et al., *Effect of Storage on Skin Allograft Survival*, Arch Surg. vol. 99, 100–102 (Jul. 1969).

Reddi, *Bone Matrix in the Solid State: Geometric Influence on Differentiation of Fibroblasts*, Adv Bio Med Phys, 1–18 (Jun. 1974).

Swaim, *Skin Grafts*, Plastic and Reconstructive Surgery, Veterinary Clinics of North America: Small Animal Practice vol. 20 No. 1, 147–175 (Jan. 1990).

Taylor, *Cryopreservation of Skin: Discussion and Comments*, Cryobiology vol. 3, No. 2, 192–196 (1966).

Wachtel, *Viability of Frozen Allografts*, American Journal of Surgery, vol. 138, 783–787 Dec. 1979).

Langdon, *Reconstitution of Structure and Cell Function in Human Skin Grafts Derived from Cryopreserved Allogeneic Dermis and Autologous Cultured Keratinocytes*, Journal Invest. Dermatology vol. 91, 478–485 (1988).

May et al., *Recent Developments in Skin Banking and the Clinical Uses of Cryopreserved Skin*, Journal of MAG, vol. 73, 233–236, (Apr. 1984).

"Porcine Heterograft Valve Replacement in Children", by D.B. Wiliams, MD, G.K. Danielson, MD, D.C. McGoon, MD, F.J. Puga, MD, D.D. Mair, MD and W.D. Edwards MD, *J. Thorac Cardiovasc Surg.* 84: pp. 446–450, Sep. 1982.

"Mechanical Testing of Cryopreserved Aortic Allografts Comparison with Xenografts and Fresh Tissue", by I. Vesely, PhD, L. Gonzalez–Lavin, MD, D. Graf and D. Goughner, MD, PhD, FRCPC, *Journal of Thoracic and Cardiovascular Surgery*, St. Louis, vol. 99, No. 1, pp. 119–123, Jan. 1990.

"An Approach to the Optimization of Preparation of Bioprosthetic Heart Valves", by D. Mavrilas and Yannis Missirlis, *J. Biomechanics*, vol. 24, No. 5 pp. 331–339, 1991.

"Residual Heteroantigencity of Glutaraldehyde–Treated Porcine Cardiac Valves", by M.L. Villa, S. DeBiasi and F. Pilotto, *Tissue Antigens*, vol. 16, pp. 62–29, 1980.

"Tissue–Derived Biomaterials and Their Use in Cardiovascular Prosthetic Devices", by S.L. Hilbert, V.J. Ferrans, and M. Jones, *Medical Progress Through Technology*, vol. 14, pp. 115–153, 1988.

"Characterization of Pepsin–Solubilized Bovine Heart–Valve Collagen", by R.I. Bashey, H.M. Bashey and S.A. Jimenez, *Biochem Journal* vol. 173, pp. 885–894, 1978.

"Collagen Heterogeneity in Pig Heart Valves", by P. Mannschott, D. Herbage, M. Weiss and C. Buffevant, *Biochimica et Biophysica Acts*. vol. 434, pp. 177–183, 1976.

"Preservation of Aortic Heart Valves with Maintenance of Cell Viability", by A.W. M. Van Der Kamp, MD, W.J. Visser, J.M. Van dongen, Ph.D., J. Nauta, MD and H. Galjaard, MD, *Journal of Surgical Research*, vol. 30, pp. 47–56, 1981.

"Viability of Connective Tissue Cells Following Storage of Aortic Valve Leaflets", by D.D. Reichenbach, MD, H. Mohri, MD, M. Sands and K.A. Merendino, MD, *Journal of Thoracic and Cardiovascular Surgery*, vol. 62, No. 5, pp. 690–695, Nov. 1971.

"Aortic Valve Replacement with Frozen Irradiated Homografts", by P. M. Beach, Jr., MD, F.O. Bowman, Jr., MD, G.A. Kaiser, MD, E. Parodi, MD and J.R. Malm, MD, Department of Surgery, College of Physicians and Surgeons, Columbia University, *Supplement I to Circulation*, vols. XLV and XLVI, pp. I–29–I 35, May 1972.

"Histological Assessment of Orthotopic Aortic Valve Leaflet Allografts: Its Role in Selecting Graft Pre–Treatment" by L.C. Armiger, J.B. Gavin and B.G. Barratt–Boyes, *Pathology*, vol. 15, pp. 67–73, 1983.

"A Comparison of Aortic Valve Replacement with Viable Cryopreserved and Fresh Allograft Valves, With a Note on Chromosomal Studies", by M.F. O'Brian, FRACS, FRCS, E. G. Stafford, FRACS, FACS, M.A.H. Gardner, FRACS, P.G. Pohlner, FRACS, D.C. McGiffin, FRACS, J.W. Kirklin, MD, *Journal of Thoracic and Cardiovascular Surgery*, vol. 94, No. 6, pp. 812–823, Dec. 1987.

"Cryopreserved Viable Allograft Aortic Valves", by M.F. O'Brien, E.G. Stafford, M.A. H. Gardner, P. Pohlner, D.C. McGrinnin, M. Johnston, P. Tesar, A. Brosnan, P. Duffy, (Prince Charles Hospital), Brisbane, Australia, pp. 311–321.

"The Viable Cryopreserved Allograft Aortic Valve", by M.F. O'Brien, FRACS, G. Stafford, FRACS, M. Gardner, FRACS, P. Pohlner, FRACS, D. McGiffin, FRACS, N. Johnston, FRACPA, A. Brosnan, B.Sc, and P. Duffy, MBBS, PhD, *J. Cardiac Surg.* vol. 1, No. 3, Supplement, pp. 153–167, 1987.

"Durability of The Viable Aortic Allograft", by W. W. Angell, MD, J.H. Oury, MD, J.J. Lamberti MD and J. Koziol, PhD, *J. Cardiovaic Surg.* vol. 98, pp. 48–56, 1989.

"Xenotransplantation: A View to the Future", by F.H. Bach, *Transplantation Proceedings*, vol. 25, No. 1, pp. 25–29, Feb. 1993.

"New Biologic and Synthetic Vascular Prostheses", by H.P. Greisler, MD, *Medical Intelligence Unit*, Chapter 3, Biohybrids—Biological Coatings In Synthetic Grafts, pp. 33–46.

"Immunological Aspects of Treated Natural Tissue Prostheses", by P.K. Bajpai, Chapter 2, vol. 1, pp. 5–25.

"Improved Endothelial Viability of Heart Valves Cryopreserved by a New Technique", by E.J. Feng, C.E. van Hove, R. Mohan, L. Andries, M. Rampart, A.G. Herman and P.J. Walter, *Eur. J. Cardio–Thoracic Surgery*, vol. 6, pp. 251–155, 1992.

"Xenografts—Future Prospects for Clinical Transplantation", by T.D.H. Cairns, D.H. Taube, N. Stevens, R. Binns and K.I. Welsch, *Immunology Letters*, vol. 29, pp. 167–170, 1991.

"Transplantation Immunology", by C.H. Kirkpatrick, MD, D.T. Rowlands, Jr., MD, *JAMA*, vol. 268, No. 20, pp. 2952–2958, Nov. 25, 1992.

"Cryopreservation Does Not Alter Antigenic Expression of Aortic Allografts", by R.P. Cochran, MD and K.S. Kunzelman, BS, *Journal of Surgical Research*, vol. 46, pp. 597–599, 1989.

"Effect of Cryopreservation on the Presence of Endothelial Cells on Human Valve Allografts", by F.M. Lupinetti, MD, T.T. Tsai, J.M. Kneebone, MS and E.L. Bove, MD, *J. Thorac Cardio–Vasc Surg*, vol. 106, pp. 912–917, 1993.

"Effects of Cell Removal Upon Heart Valve Leaflet Mechanics and Immune Responses in a Xenogeneic Model", by S. Goldstein & K. Brockbank, *Poster Abstracts*, P29.

"Lack of Cross–Species Sensitization Between Skin Allo–and Xenotransplants in Mice", by C. Vizler, T. Janossy, Z. Tabi, P. Vegh, Institute of Experimental Surgery, *Poster Abstracts*, P30.

"Failure of Cryopreserved Homograft Valved Conduits in the Pulmonary Circulation", by D.C. Cleveland, MD, W.G. Williams, MD, A.J. Razzouk, MD, G.A. Trusler, MD, I.M. Rebeyka, MD, L. Duffy, PhD, Z. Kan, MD, J.G. Coles, MD and R.M. Freedom, MD, (circulation from the Divisions of Cardiovascular Surgery and Cardiology, The Hospital for Sick Children, II pp. 150–153).

"Degeneration of Aortic Valve Allografts in Young Recipients", by D. R. Clarke, MD, D.N. Campbell, MD, A.R. Hayward, MD, PhD and D.A. Bishop, BS, *J. Thorac Cardiovasc Surg*, vol. 105, pp. 934–942 1993.

"Immunogenicity of Tanned Tissue Valve Xenografts" by P.K. Bajpai, *Biomaterials in Cardiovascular Surgery, General Surgery and Neurosurgery*, Chapter 47, pp. 735–752.

"Xenotransplantation: A Current Perspective", by F.H. Bach, A.P. Dalmasso and J.L. Platt, *Transplantation Reviews*, vol. 6, No. 3, pp. 163–174, Jul. 1992.

"Endothelial Cell Replication in an InVivo Model of Aortic Allografts", by F.M. Lupinetti, MD, T.T. Tsai, and J.M. Kneebone, MS, *Ann Thorac Surg*, vol. 56, pp. 237–241, 1993.

"Endothelial Cell Growth Factor Attachment to Biomaterials", by H.P. Greisler, J. Klosak, J.W. Dennis, J. Ellinger, D.U. Kim, W. Burgess and T. Maciag, *Trans Am Soc Artif Intern Organs*, vol. XXXII, pp. 346–349, 1986.

"Biomaterial pretreatment with ECGF to Augment Endothelial Cell Proliferation", by H.P. Greisler, MD, J.J. Klosak, M.D., J.W. Dennis, MD, S.M. Karesh, PhD, J. Ellinger and D.U. Kim, MD, *Journal of Vascular Surgery*, pp. 393–402.

"Endothelial Cell–seeded Artificial Prostheses for Coronary Bypass Grafting", by T.J. Hunter, S.P. Schmidt, W.V. Sharp, R.F. Debski, M. M. Evancho, R.E. Clarke, and L. J. Falkow, *Trans Am Soc Artif Intern Organs*, vol. XXXII, pp. 339–341, 1986.

"In Vitro Cultivation and Immunogenicity of Human Cardiac Valve Endothelium", by A. Simon, MD, N. Zavazava, MD, PhD, H.H. Sievers, MD, PhD and W. Muller–Ruchholtz, MD, PhD., *J. Card Surg*, vol. 8, pp. 656–665, 1993.

"Human Xenoreactive Natural Antibodies—Avidity and Targets on Procine Endothelial Cells", *Transplantation—Brief Communication*, vol. 56, pp. 1251–1292, Nov. 1993.

"Properties of Acellular Vascular Matrix", by R.C. Duhamel, K. Brendel, R.L. Reinert, J.M. Malone, Conference Paper; Conference entitled Biomaterials '84: Transactions—Second World Congress on Biomaterials, 10th Annual Meeting of the Society for Biomaterials, Sixteenth International Biomaterials Symposium—Washington, DC. Published by Soc for Biomaterials, San Antonio, TX, p. 98, 1984.

"A Gelatin Membrane Substrate for the Transplantation of Tissue Cultured Cells", by M.M. Jumblatt, B.D. Schwartz, *Transplantation (USA)*, pp. 498–499, 1980.

"Lifecell Corp: LifeCell begins Clinical Evaluation of its Processed Human Skin, AlloDerm", Byline: Business Editors, *The Woodlands, Texas (Business Wire)*, Aug. 17, 1992.

"Heterologous Heart Valves: Past, Present, and Future", by S.O. Burman, MD, *Ann Thorac Surg*, vol. 48, 1989.

"Discordant Xenografting: A Summary and Look to the Future", by F.H. Bach, *Transplantation Proceedings*, vol. 24, No. 2 pp. 739–742, Apr. 1992.

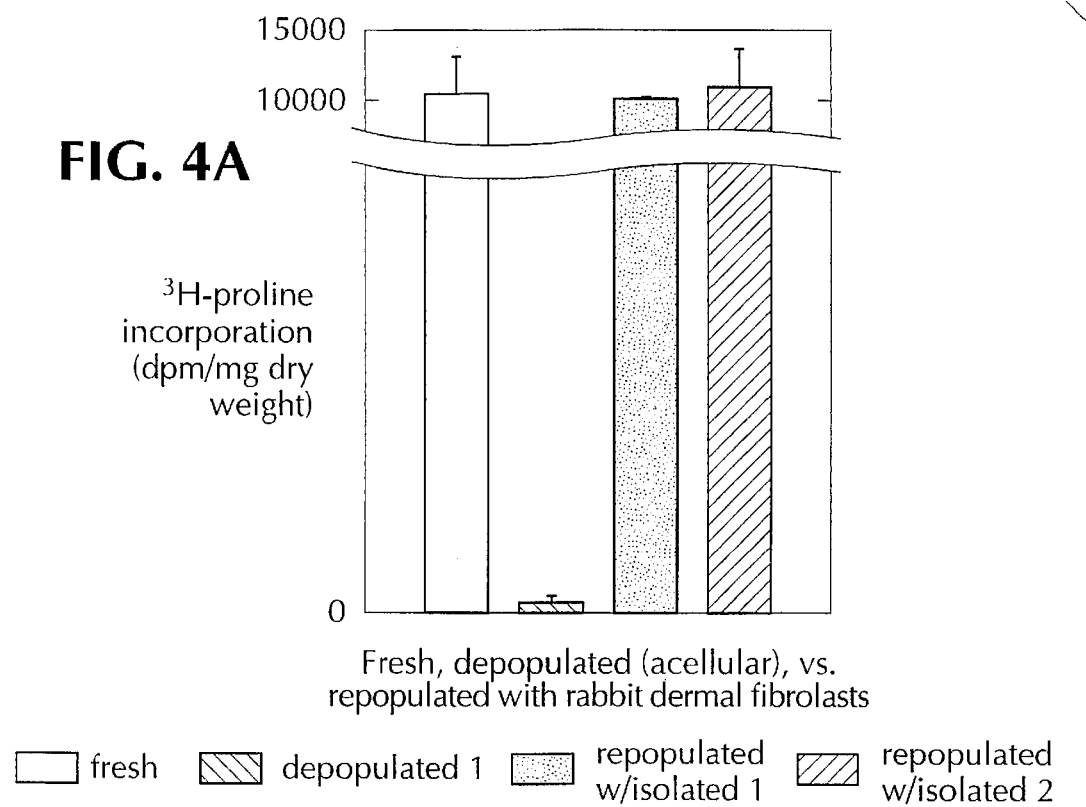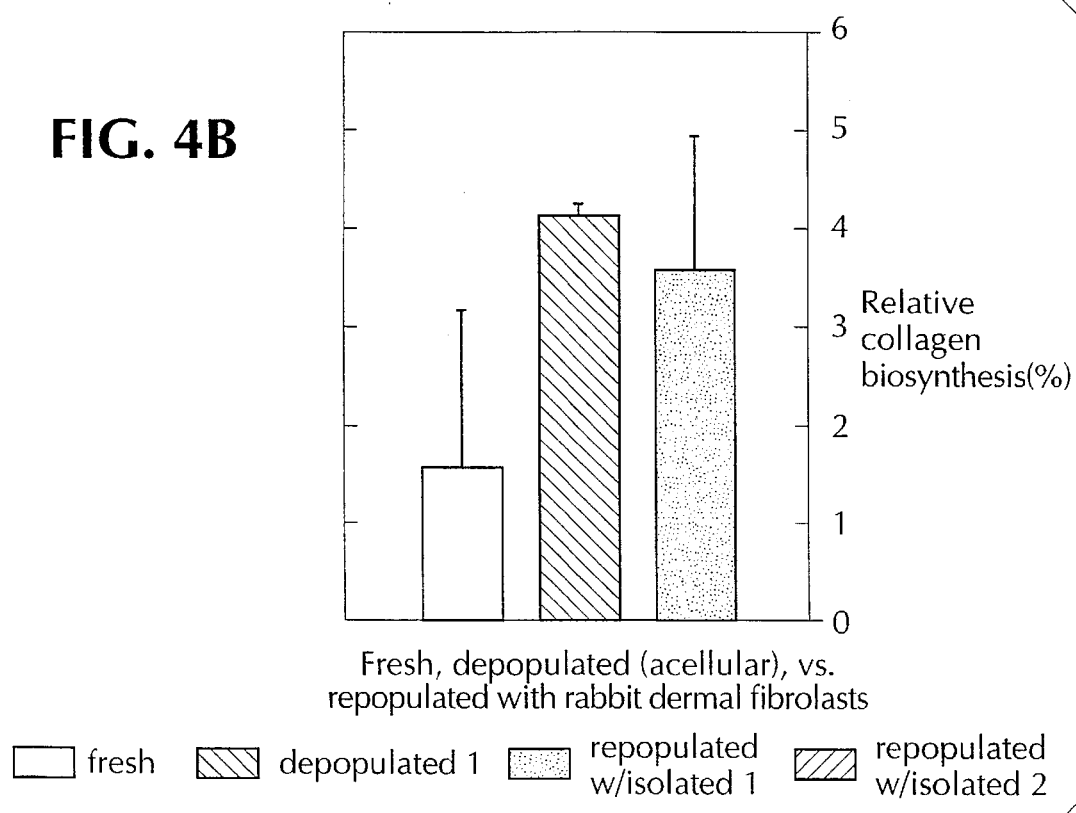

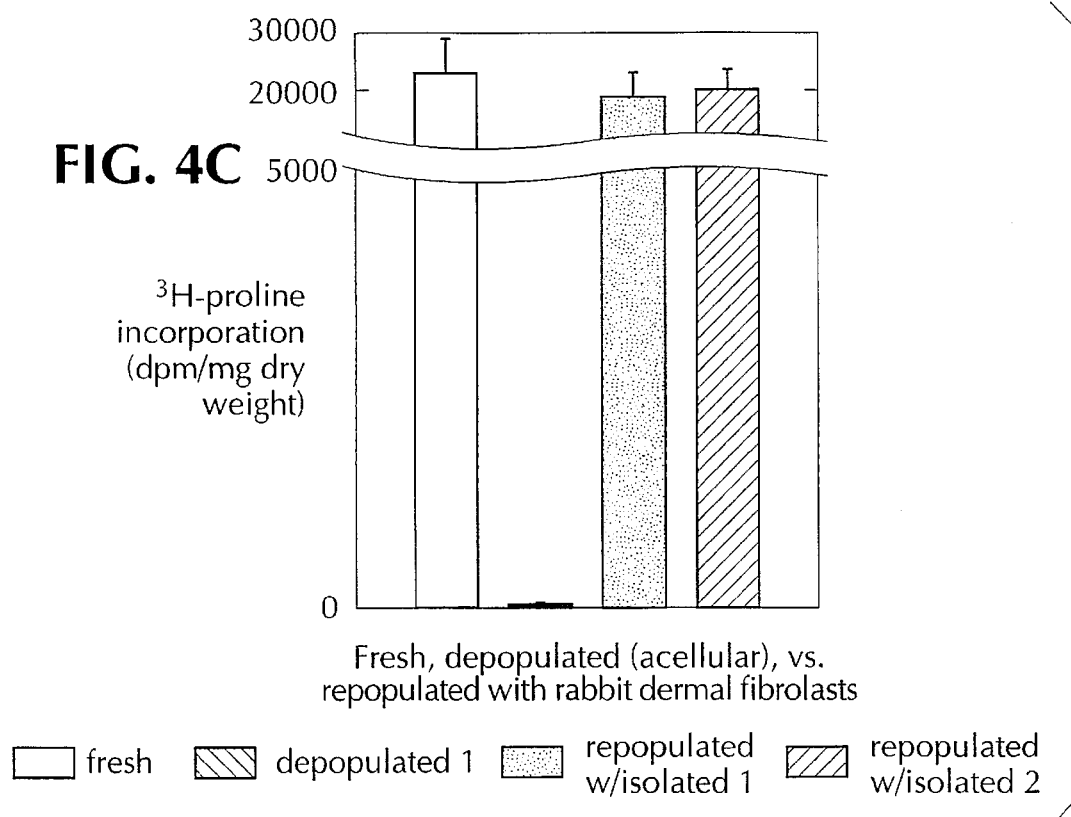
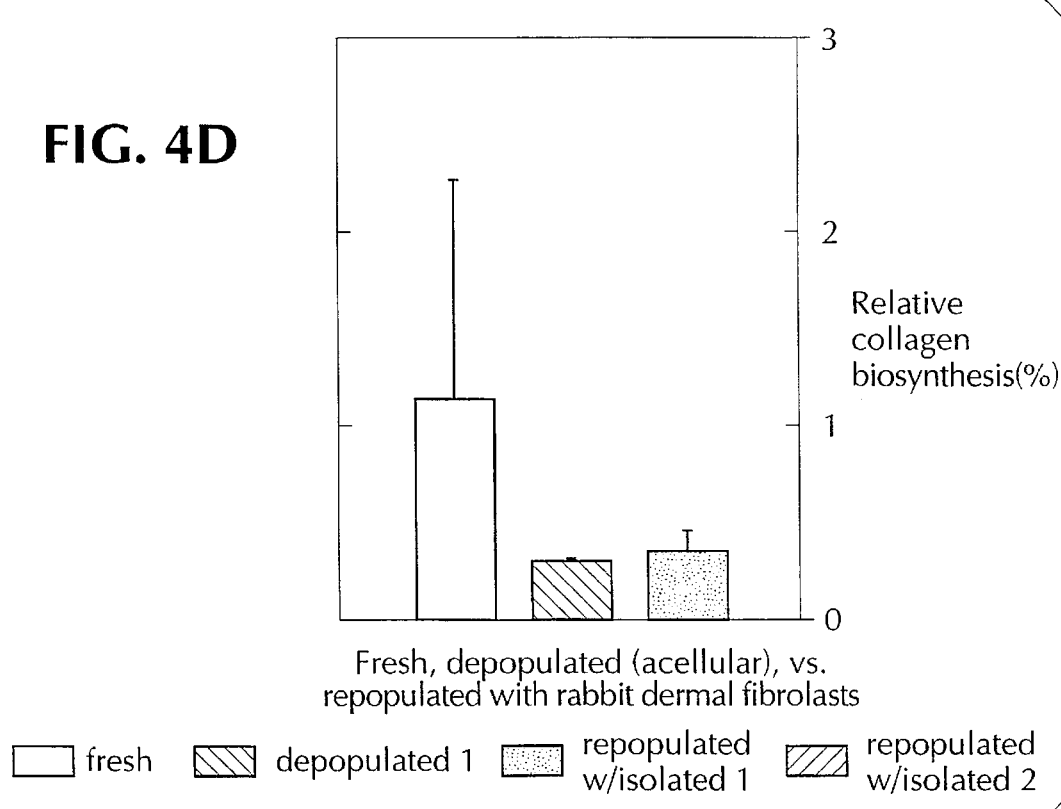

FIG. 10A

| | Fresh | Cryopreserved | Depopulated (37°C) | Depopulated (4°C) |
|---|---|---|---|---|
| Tissue Modulus | 43.8±8.3 | 35.8±7.0[a] | 58.3±7.6[a] | 46.0±8.2[a] |
| Ultimate Tensile Strength | 7.4±1.6 | 5.9±1.1[a] | 10.7±1.3[a] | 9.1±1.5[a] |
| Toughness (resilience) | 1.6±0.3 | 1.5±0.4[a] | 2.5±0.5[a] | 2.6±0.6[a] |
| Strain at Fracture % | 43.7±4.5 | 44.2±7.3[a] | 57.7±8.1[a] | 67.5±5.0[a] |

Units of $MN/m^2$. Mean ± SEM. n, Fresh (8), Cryopreserved (8), Depopulated at 37°C (13), and Depopulated at 4°C (5). [a] Difference not significant compared to fresh tissue.

FIG. 10B

|  | Fresh | Cryopreserved | Depopulated (37°C) | Depopulated (4°C) |
|---|---|---|---|---|
| Tissue Modulus | 4.9±0.4 | 5.2±0.9[a] | 5.1±1.3[a] | 7.7±2.9[a] |
| Ultimate Tensile Strength | 0.9±0.07 | 0.9±0.2[a] | 1.2±0.3[a] | 1.2±0.2[a] |
| Toughness (resilience) | 0.4±0.03 | 0.6±0.2[a] | 1.5±0.3[b] | 0.8±0.1[b] |
| Strain at Fracture % | 117±8.7 | 96.4±11.5[a] | 161±26.4[a] | 112±41.9[a] |

Units of MN/m². Mean ± SEM. n, Fresh (8), Cryopreserved (5), Depopulated at 37°C (7), and Depopulated at 4°C (3). [a] Difference not significant compared to fresh tissue.
[b] Difference significant at $p < 0.05$ compared to fresh tissue.

TREATED TISSUE FOR IMPLANTATION AND METHODS OF PREPARATION

This application is a division of application Ser. No. 08/213,754, filed on Mar. 14, 1994.

BACKGROUND

Surgical heart valve replacement may involve implantation of one of three distinct prosthesis types; mechanical (synthetic), bioprosthetic (chemically-fixed porcine valve or bovine pericardium), or human allograft. These prostheses provide effective hemodynamic improvement for replacement of native aortic valves that are either congenitally malformed or have been damaged by degenerative changes or disease resulting in either aortic insufficiency or aortic stenosis. Of the approximately 55,000 aortic valve implants annually in the U.S., 75% are mechanical valves. The remainder of the replacements are of transplanted tissues. Of these, over 80% are porcine bioprostheses; the relatively small number of allografts (2,500 per year) is primarily due to their limited availability.

The criteria for an ideal prosthesis would include natural hemodynamics, long-term durability, low incidence of thromboembolic complications, freedom from calcification, proven lack of immunogenicity and no inappropriate hyperplastic responses following implantation. Even in autologous transplant situations, the surgical handling of the tissue, such as vein grafts, may itself be a stimulus for tissue hyperplasia and subsequent failure of the graft.

In accordance with this invention, heart valves, pulmonary and aortic, may be prepared having advantageous properties with respect to wear, tendency to calcify, stimulation of immune responses, and reduced difficulty in acquisition. It is also applicable to other forms of tissues particularly those composed of structural interstitial collagens.

Various synthetic grafts and mechanical organs have been developed and are currently in use. However, these synthetic replacements are known to be subject to embolic complications or decreases in material strength over long periods of implantation. Although structural modifications in mechanical prostheses such as heart valves have been improved with respect to their wear characteristics, they remain liable to valve malfunction, which may occur suddenly and without warning, resulting in emergency situations requiring surgical intervention and replacement of the artificial prosthetic device. Because of the surface properties of synthetic/mechanical prostheses used in the vasculature, platelet adhesion increases the likelihood of thrombus formation and anticoagulant therapy must be provided for the life of the implant and makes such implants undesirable for certain groups of potential recipients (for example, women of child-bearing years).

One alternative, bioprosthetic heart valves, are prepared from valve tissues of porcine or bovine origin. Because these are species discordant immunologically from man, they are rapidly rejected by the implant recipient despite the use of immunosuppression drug therapy that would otherwise maintain an allograft. Significantly, these tissues are liable to hyperacute rejection by the recipient because of the presence in the recipient of preformed natural antibodies which recognize antigens on the surface of foreign cells, particularly those of the endothelial lining of heart valves and blood vessels. While bovine or porcine valve tissues are structurally and biomechanically appropriate for use in humans, the potential of such foreign tissue to stimulate immune rejection in the recipient has in the past dictated treatments with chemical cross-linking agents such as glutaraldehyde. Such treatment of the tissue reduces the stimulation of an immunological response by the recipient to the foreign tissue, and also stabilizes the collagen protein of the resulting non-viable valve tissue making it more resistent to degradation by proteolytic enzymes. However, because these tissue grafts are non-viable, there is no biosynthetic mechanism to repair structural proteins broken down during the operation of the tissue in the recipient. Such tissue grafts tend to calcify with time, increasing the risk of structural damage and consequential failure. While occurring with less frequency relative to mechanical grafts, thromboembolism is also a patient management issue for recipients of these grafts.

Similarly, organs such as kidneys have been transplanted allogeneically from one sibling to another in an effort to minimize immunologically mediated reactions in the transplant recipient, which would result in organ rejection. These patients, as well as patients receiving transplant organs from donors other than a sibling, are frequently administered drugs to suppress their immune system. While the immunological response to transplant tissue or organs may be suppressed through the use of immunosuppressant drugs to minimize rejection, immunosuppressant therapy is general in nature. Hence, immunosuppressant drugs also tend to suppress the immune response generally, which reduces the transplant recipient's ability to combat infection.

More recently processes have been described for generating improved bioprosthesis for human or mammalian implant, by treatment of non-human tissue. See, Orton, E. Christopher, U.S. Pat. No. 5,192,312. Orton discloses generation of implant tissue by removing native cells from tissue of, for example, porcine origin; and then, repopulating the tissue with new cells in the presence of growth factor. The repopulating cells are immunologically compatible with the intended implant recipient. The biografts produced by this process are free from many of the disadvantages of other prior art bioprosthesis.

SUMMARY OF THIS INVENTION

This invention provides new and advantageous processes for generating implant tissue suitable for implant in humans or other meals. The process of this invention generally relates to treatment of xenogeneic or allogeneic tissue to generate a viable bioprothesis which does not produce an adverse immune response by the recipient upon implant, and possesses the regenerative capabilities of allografts, while exhibiting only limited propensity to calcify and little stimulation of thromboembolism.

In accordance with the foregoing, the process of this invention includes the steps of preparing a xenogeneic (or allogeneic) tissue matrix for further processing by removing native cells and other antigens and cellular debris from the decellularized tissue matrix, and treating the matrix to inhibit generation of new immunological sites. This tissue matrix is then treated with the cellular adhesion factors described below to enhance attachment of cells to the matrix during the process of repopulating the tissue matrix with such new cells.

Depending upon the cells used to repopulate the natural tissue matrices, differing properties of the species hybrid bioprosthesis may be obtainable, such as the ability to synthesize proteins otherwise atypical for the natural tissue at the site of implantation or unique to certain age groups. These hybrid grafts would combine the structural advantages of bioprosthetic grafts with the functional and regenerative capabilities of allografts as well as display attenuated or no immune response, limited propensity to calcify, and little stimulation of thromboembolism. As with all bioprosthetic grafts currently in use, these modified tissues would not be supply limited and would afford the functionality of the graft to more recipients. In addition, these grafts would not be necessarily chemically altered to make them stable to the recipient's immune system; therefore, such materials would display biomechanical properties more like those of the tissue they are used to replace.

The invention described herein is useful for generating bioprosthetic xenografts suitable for human implantation. It is particularly well suited for generating xenogeneic grafts in which the major structural component is connective tissue matrix, such as heart valves, particularly heart valves of porcine or bovine origin. Examples of other tissues suitable for use in this invention may be, but are not limited to, aortic heart valves, pulmonary heart valves, fascia lata, dura mater, pericardium, meniscus, skin, ligament, tendon, and other connective tissue structures.

BRIEF DESCRIPTION OF THE DRAWINGS

FIG. 4a. Total Protein Synthesis in Porcine Aortic Heart Valve Leaflets.

FIG. 4b. Collagen Protein Synthesis in Porcine Aortic Valve Leaflets.

FIG. 4c. Total Protein Synthesis in Porcine Aortic Valve Leaflets.

FIG. 4d. Collagen Protein Synthesis in Porcine Aortic Valve Leaflets.

FIG. 10a. Tensile Failure Data for Porcine Aortic Valve Leaflets.

FIG. 10b. Tensile Failure Data for Porcine Aortic Valve Leaflets.

DETAILED DESCRIPTION OF THE INVENTION

Figure 1:
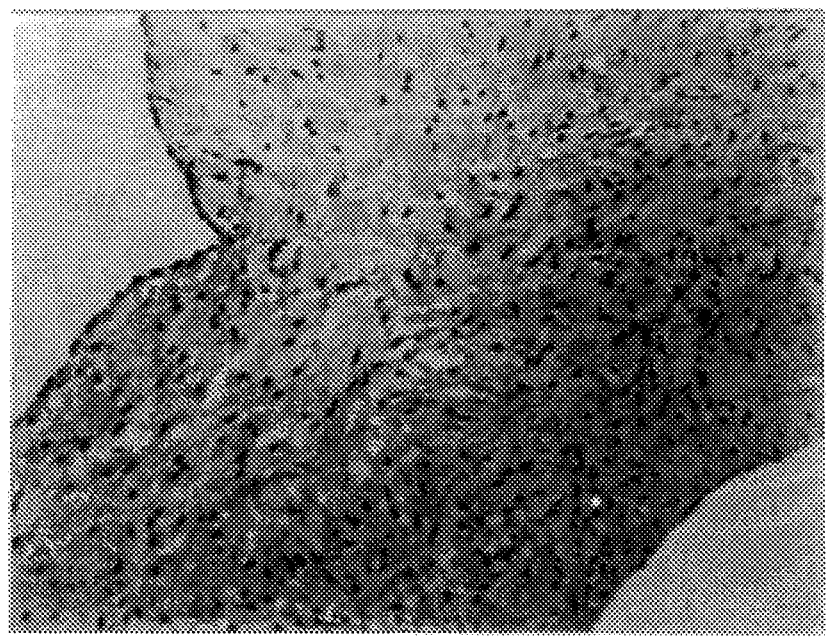
FIG. 1. Photomicrograph of a fresh aortic leaflet.

Depending on the type of transplant intended, if the recipient is human, the initial transplant tissue or organ may be of non-human origin. These tissues or organs may be obtained at approved slaughterhouses from animals fit for human consumption or from herds of domesticated animals maintained for the purpose of providing these tissues or organs. The tissues or organs are handled in a sterile manner, and any further dissection of the tissue or organs is carried out under aseptic conditions.

Transplant tissue originating from a non-human sources and intended for use in a human recipient may be processed to generate a hybrid xenograft or xenogeneic implant tissue, which is formed from a non-human tissue matrix, free of native cells and other antigenic components and which is populated with viable human cells. The steps of the process for generating such immunologically tolerable implants are described below.

After collection and dissection, the transplant tissue may be sterilized by incubating it in a sterile buffered nutrient solution containing antimicrobial agents, for example an antibacterial, an antifungal, or a sterilant compatible with the transplant tissue.

The sterilized transplant tissue may then be cryopreserved for further processing at a later time or may immediately be further processed according to the next steps of this process including a later cryopreservation of the tissue matrix or other tissue products of the process.

Decellularization

A preliminary step of this invention calls for elimination of native viable cells as well as other cellular and acellular structures or components which may elicit an adverse immune response by the implant recipient.

Several means of reducing the viability of native cells in tissues and organs are known, including physical, chemical, and biochemical methods. See, e.g. U.S. Pat. No. 5,192,312 which is incorporated herein by reference. Such methods may be employed in accordance with the process described herein. However, the decellularization technique employed should not result in gross disruption of the anatomy of the transplant tissue or substantially alter the biomechanical properties of its structural elements. The treatment of the tissue to produce a decellularized tissue matrix should also not leave a cytotoxic environment that mitigates against subsequent repopulation of the matrix with cells allogeneic or autologous with respect to the recipient. Cells and tissues that are allogeneic for the recipient are those that originate with or are derived from a donor of the same species as the recipient. Autologous cells or tissues are those that originate with or are derived from the recipient.

Physical forces, for example the formation of intracellular ice, can be used to decellularize transplant tissues. For example, vapor phase freezing (slow rate of temperature decline) of intact heart valves can reduce the cellularity of the heart valve leaflets as compared to liquid phase freezing (rapid). However, slow freezing processes, in the absence of cryoprotectant, may result in tissue disruption such as the cracking of heart valve conduits. Colloid-forming materials may be added during freeze-thaw cycles to alter ice formation patterns in the tissue. Polyvinylpyrrolidone (10% w/v)

and dialyzed hydroxyethyl starch (10% w/v) may be added to standard cryopreservation solutions (DMEM, 10% DMSO, 10% fetal bovine serum) to reduce extracellular ice formation while permitting formation of intracellular ice. This allows a measure of decellularization while affording the collagenase tissue matrix some protection from ice damage. Additionally, it is noted, that tissues, particularly heart valve conduits, will crack if rapidly frozen irrespective of the presence of cryoprotectant.

Alternatively, various enzymatic or other chemical treatments to eliminate viable native cells from implant tissues or organs may be used. For instance, extended exposure of cells to proteases such as trypsin result in cell death. However, because at least a portion of the type I collagen molecule is sensitive to a variety of proteases, including trypsin, this may not be the approach of choice for collagenous grafts intended for implant in high mechanical stress locations.

Combinations of different classes of detergents, for example, a nonionic detergent, Triton X-100, and an anionic detergent, sodium dodecyl sulfate, may disrupt cell membranes and aid in the removal of cellular debris from tissue. However, steps should be taken to eliminate any residual detergent levels in the tissue matrix, so as to avoid interference with the later repopulating of the tissue matrix with viable cells.

The decellularization of the transplant tissue is preferably accomplished by the administration of a solution effective to lyse native cells in the transplant tissue. Preferably, the solution may be an aqueous hypotonic or low ionic strength solution formulated to effectively lyse the native tissue cells. Such an aqueous hypotonic solution may be de-ionized water or an aqueous hypotonic buffer. Preferably the aqueous hypotonic buffer may contain additives that provide sub-optimal conditions for the activity of selected proteases, for example collagenase, which may be released as a result of cellular lysis. Additives such as metal ion chelators, for example 1,10-phenanthroline and ethylenediaminetetraacetic acid (EDTA), create an environment unfavorable to many proteolytic enzymes. Providing sub-optimal conditions for proteases such as collagenase, may assist in protecting the tissue matrix from degradation during the lysis step. Particularly, suboptimal conditions for proteases may be achieved by formulating the hypotonic lysis solution to eliminate or limit the amount of calcium and zinc ions available in solution. Many proteases are active in the presence of calcium and zinc ions and lose much of their activity in calcium and zinc ion free environments.

Preferably, the hypotonic lysis solution will be prepared selecting conditions of pH, reduced availability of calcium and zinc ions, presence of metal ion chelators and the use of proteolytic inhibitors specific for collagenase, such as $\beta_1$-anticollagenase, such that the solution will optimally lyse the native cells while protecting the underlying tissue matrix from adverse proteolytic degradation. For example a hypotonic lysis solution may include a buffered solution of water, pH 5.5 to 8, preferably pH 7 to 8, free from calcium and zinc ions and including a metal ion chelator such as EDTA. Additionally, control of the temperature and time parameters during the treatment of the tissue matrix with the hypotonic lysis solution, may also be employed to limit the activity of proteases.

It is preferred that the decellularization treatment of the tissue matrix also limits the generation of new immunological sites. While collagen is typically substantially non immunogenic, partial enzymatic degradation of collagen may lead to heightened immunogenicity. Accordingly, a preferable step of this process includes treatment of the tissue with enzymes, such as nucleases, effective to inhibit cellular metabolism, protein production and cell division without degrading the underlying collagen matrix. Nucleases that can be used for digestion of native cell DNA and RNA include both exonucleases and endonucleases. A wide variety of which are suitable for use in this step of the process and are commercially available. For example, exonucleases that effectively inhibit cellular activity include DNAase I (SIGMA Chemical Company, St. Louis, Mo.) and RNAase A (SIGMA Chemical Company, St. Louis, Mo.) and endonucleases that effectively inhibit cellular activity include EcoR I (SIGMA Chemical Company, St. Louis, Mo.) and Hind III (SIGMA Chemical Company, St. Louis, Mo.).

It is preferable that the selected nucleases are applied in a physiological buffer solution which contains ions which are optimal for the activity of the nuclease, such ions include magnesium and calcium salts. It is also preferred that the ionic concentration of the buffered solution, the treatment temperature and the length of treatment are selected to assure the desired level of effective nuclease activity. The buffer is preferably hypotonic to promote access of the nucleases to the cell interiors. For treatment of endogenous endothelial cells of non-human heart valve tissue, particularly valves of porcine or bovine origin the tissue is preferably treated with a physiologically buffered medium comprised of nucleases DNAase I and RNAase A. Preferably, the nuclease degradation solution contains about 0.1 µg/ml to 50 µg/ml, preferably 10 µg/ml, of the nuclease DNAase I, and 0.1 µg/ml to 10 µg/ml, preferably 1.0 µg/ml, of RNAase A. The tissue may be decellularized by application of the foregoing at a temperature of about 20° C. to 38° C., preferably at about 37° C. for about 30 minutes to 6 hours, while at the same time the generation of new immunological sites as a result of collagen degradation is limited.

Other enzymatic digestions may be suitable for use herein, for example, enzymes that will disrupt the function of native cells in a transplant tissue may be used. For example, phospholipase, particularly phospholipases A or C, in a buffered solution, may be used to inhibit cellular function by disrupting cellular membranes of endogenous cells. Preferably, the enzyme employed should not have a detrimental effect on the tissue matrix protein. The enzymes suitable for use may also be selected with respect to inhibition of cellular integrity, and also include enzymes which may interfere with cellular protein production. The pH of the vehicle, as well as the composition of the vehicle, will also be adjusted with respect to the pH activity profile of the enzyme chosen for use. Moreover, the temperature applied during application of the enzyme to the tissue should be adjusted in order to optimize enzymatic activity.

Subsequent to the chosen decellularization treatment, the resultant transplant tissue matrix is washed to assure removal of cell debris which may include cellular protein, cellular lipids, and cellular nucleic acid, as well as any extracellular debris such as extracellular soluble proteins, lipids and proteoglycans. Removal of this cellular and extracellular debris reduces the likelihood of the transplant tissue matrix eliciting an adverse immune response from the recipient upon implant. For example, the tissue may be incubated in a balanced salt solution such as Hanks' Balanced Salt Solution (HBSS). The composition of the balanced salt solution wash, and the conditions under which it is applied to the transplant tissue matrix may be selected to diminish or eliminate the activity of the nuclease or other enzyme utilized during the decellularization process. Such a balanced salt wash solution would preferably not contain magnesium or calcium salts, and the washing process may include incubation at a temperature of between about 2° C. and 42° C., with 4° C. most preferable. The transplant tissue matrix may be incubated in the balanced salt wash solution for up to 10 to 12 days, with changes in wash solution every second or third day. Optionally, an antibacterial, an antifungal or a sterilant or a combination thereof, may be included in the balanced salt wash solution to protect the transplant tissue matrix from contamination with environmental pathogens.

Where the tissue being prepared for transplantation by the process of this invention is skin, the decellularized tissue matrix may be utilized without the subsequent steps of in vitro cellular repopulation. The decellularized and substantially non-immunogenic tissue matrix, is suitable for implant into a recipient. The reduced immunogenicity of the skin tissue matrix will increase the tolerance of the transplanted skin by the recipient's immune system. The implant may then be repopulated in vivo by the implant recipient's own cells. Prior to use as a skin graft, the skin matrix may be treated to enhance the ingrowth and attachment of the recipient's own skin cells. For instance, the matrix may be treated with adhesion factors or growth factors, such as keratinoctye growth factor, or both, to enhance the infusion of keratinocytes.

The tissue matrix prepared in accordance with the above is free of its native cells, and additionally cellular and extra-cellular antigen components have been washed out of the tissue matrix. Preferably the tissue matrix has been treated in a manner which limits the generation of new immunological sites in the collagen matrix. The tissue matrix, however, retains the essential biomechanical strength necessary to provide the framework for further processing of the matrix.

The tissue matrix processed according to this invention may be cryopreserved for later use. Cryopreservation of decellularized transplant tissue would assure a supply or inventory of substantially non-immunogenic tissue matrices which, upon thawing, would be ready for further treatment according to the subsequent steps of this invention, or further processed as desired to provide an implant tissue product. For example, tissue matrices may be inventoried until such time as the particular cells to be employed during repopulation are identified. This may be of particular utility when the tissue matrix is to be repopulated with cells derived from the recipient or other cells selected for use based on their immunological compatibility with a specific recipient.

It is also envisioned that native transplant tissue may be cryopreserved prior to undergoing any of the processes of this invention. Tissues which are not decellularized retain their native cells in conjunction with the collagenous tissue matrix. Upon thawing these tissues may be further processed. Beneficially, the cryopreservation of intact transplant tissue may also aid in the depopulation of the tissue as a result of cellular death brought on by cryopreservation.

Techniques of cryopreservation of tissue are well known in the art. Brockbank, K. G. M. *Basic Principles of Viable Tissue Preservation.* In: *Transplantation Techniques and Use of Cryopreserverd Allograft Cardiac Valves and Vasular Tissue.* D. R. Clarke (ed.), Adams Publishing Group, Ltd., Boston. pp 9–23, discusses cryopreservation of tissues and organs and is hereby incorporated by reference.

The tissue matrix, whether or not having been cryopreserved, may be next treated to enhance the adhesion and inward migration of the allogeneic or autologous cells, in vitro, which will be used to repopulate the transplant tissue.

Cell Adhesion

While not wishing to be bound by theory, there are several factors believed to effect the attachment of cells to tissue. For example, the adherence of fibroblasts to tissue surfaces involves interactions between the cell membrane and extracellular matrix components of native tissue such as fibrillar and sheet-forming collagen, proteoglycans, and glycoproteins. In vitro, dermal fibroblasts cultured without serum attach rapidly and equally to types I and IV collagen. The extent of attachment is increased by the addition of serum (human or fetal bovine, maximal binding with 1% serum) and by purified fibronectin to the culture medium. Each of the two homologous subunits of fibronectin has two cell recognition regions, the most important of which has the Arg-Gly-Asp (RGD) sequence. A second site, binding glycosaminoglycans, acts synergistically and appears to stabilize the fibronectin-cell interactions mediated by the RGD sequence. Heparin sulfate along with chondroitin sulfate are the two glycosaminoglycans identified on cell surfaces. Heparin sulfate is linked to core proteins (syndecan or hyaluronectin) which can either be integral or membrane spanning. Cellular binding sites for extracellular matrix glycoproteins are called integrins and these mediate tight binding of cells to the adhesion factors. Each adhesion factor appears to have a specialized integrin although a single integrin may bind to several extracellular matrix factors. Fibroblasts, when adherent to intact fibronectin (cell and heparin-binding domains) display a contracted morphology with focal adhesions. Without the heparin binding domain, fibroblasts will spread but fail to develop focal adhesions.

Thus, a combination of factors may determine the rate at which cells can bind to a tissue surface. Many of these are fibroblast products, although some like fibronectin may be derived from serum supplementation as well. The rate at which these factors are expressed and secreted by cells will affect the attachment of cells to surfaces, and cytokines such as fibroblast growth factor and transforming growth factor-β are positive regulators of fibroblast collagen and fibronectin production.

It is believed that the effective attachment of cells to the tissue matrix is promoted by the interaction between the cell membrane, and extracellular components associated with the corresponding implant tissue. Accordingly, for a given cell type, and tissue type chosen for use, appropriate treatments which promote cellular attachment to the decellularized tissue matrix include treatment with extracellular tissue components and, particularly, extracellular proteins, such as glycoproteins and/or proteoglycans or glycosaminoglycans which are effective to promote attachment of cells to the decellularized tissue matrix. Accordingly, a preferred technique for repopulating the tissue matrix with cells is carried out by first treating the decellularized tissue matrix with cellular attachment factor effective to promote the attachment of the repopulating cells to the decellularized matrix.

For example, the decellularized tissue matrix may be incubated in nutrient solution containing extracellular matrix protein such as fibronectin and a glycosaminoglycan for a period effective for binding of the fibronectin to surfaces of the transplant tissue matrix to be repopulated. Preferred buffers for use with fibronectin/ glycosaminoglycan include sodium phosphate/glycerin/ bovine serum albumin (Fetal Bovine Serum, BIO-WHITTAKER) and Dulbecco's Modified Eagle's Medium (DMEM), (GIBCO). These buffers typically are used to provide a physiological acceptable pH of about 7.0 to 7.6. The presence of the extracellular matrix proteins establish a surface on the tissue matrix to which the cells that have been chosen to repopulate the matrix attach. The stimulus of the extracellular matrix protein promotes cell repopulation in the graft.

The preferred extracellular matrix protein for use herein is the intact molecular form of fibronectin (Human Plasma Fibronectin, UPSTATE Biotechnology, Inc.). This heterofunctional glycoprotein has affinity for extracellular matrix proteins, proteoglycans, and certain cell types. The fibronectin treatment solution preferably also contains a proteoglycan which may be which may be one of the glycosaminoglycans heparin, heparin sulfate, chondroitin, chondroitin sulfate, dermatin, or dermarin sulfate. It is believed that the glycosaminoglycan promotes and stabilizes the binding between fibronectin and the tissue matrix associated collagen. The matrix advantageously is capable of interaction with fibronectin because it is not chemically cross-linked.

A source of fibronectin is from human blood, processed to limit contamination with virus. The preferred glycosaminoglycan is heparin. The concentration of glycoprotein used as the adhesion factor to treat the tissue matrix may range from about 1 to about 100 µg/ml, with a fibronectin concentration of 10 µg/ml being preferred. The preferred weight ratio of fibronectin to heparin is about 10 parts fibronectin to about 1 part glycosaminoglycan, e.g. heparin. This is optimal for repopulation of porcine heart valve leaflets, but may range from about 0.1:1 to about 10:0.1 depending on the tissue used.

Preferably the components of the nutrient solution containing the adhesion factors are selected such that the solution is compatible with growth factors which are later added to the nutrient medium that the transplant tissue matrix is incubating in. These growth factors are employed to facilitate cell growth and repopulation of the tissue matrix.

Cell Repopulation

An important aspect of this invention is that the decellularized transplant tissue matrix may be repopulated with cells in vitro. The cells employed to repopulate the decellularized matrix may be allogeneic cells cultured from the same species as the intended implant recipient, or may be autologous cells cultured from the implant recipient. In either case, the autologous or allogeneic cells in the repopulated tissue matrix, known as a heterograft or chimeric graft, will elicit less of an adverse immune response than an unprocessed xenogeneic transplant tissue.

It is also envisioned that cells employed to repopulate the decellularized matrix may be cells that have been genetically manipulated to enhance the production of specific proteins. Numerous recombinant DNA technologies are known in the art for altering, enhancing, and modifying cell metabolism.

Repopulation may be accomplished by incubating the tissue matrix treated with cell adhesion factors in a nutrient medium containing the cells and growth factors active to promote cell proliferation and, hence, repopulation of the tissue matrix. A preferred cell type for use herein is fibroblast cells.

A variety of substances may be employed to enhance cell chemotaxis, increasing the rate of directional movement along a concentration gradient of the substance in solution. With respect to fibroblast cells, fibroblast growth factor, platelet-derived growth factor, transforming growth factor-β, and the substrate-adhesion molecules, fibrillar collagens, collagen fragments, and fibronectin are chemotactic for fibroblasts. In contrast to cell adhesion, fibroblast migration requires de novo protein synthesis; protein synthesis in normal fibroblastic cells is stimulated by adhesion of cells to fibronectin, so the processes of cell adhesion and cell migration during repopulation are believed to be interrelated.

Cellular migration also allows cells to move through the tissue matrix repopulating interior interstitial spaces as well as the surfaces of the tissue transplant matrix.

The number of cells required to fully repopulate particular transplant tissue matrices depends upon the volume of the tissue used and the types of cells provided. However, concentrations of 20,000 to 125,000 fibroblasts per milliliter may provide suitable coverage of the heart valve leaflet and aortic conduit tissue.

Cell Proliferation

The steps of cellular repopulation of the tissue matrix preferably are conducted in the presence of growth factors effective to promote proliferation of the cultured cells employed to repopulate the matrix. For example, when fibroblast cells are employed, a growth factor for use herein may be fibroblast growth factor (FGF), most preferably basic fibroblast growth factor (bFGF) (Human Recombinant bFGF, UPSTATE Biotechnology, Inc.).

The fibroblast growth factors (heparin-binding) are a family of mitogens active on mesenchymal cells. FGFs are not detected free in conditioned medium, instead the FGFs are found in the extracellular matrix in association with heparin sulfate, localizing in the fibronectin-heparin layer prebound to the transplant tissue matrix. The glycosaminoglycans stabilize FGF activity and are required for FGF binding to cell surface receptors where they stimulate autocrine/paracrine growth.

The matrix and cells are preferably exposed to bFGF continuously during the repopulation step to provide for stimulation of cell replication and expression of collagen protein synthesis, as required for normal valve function. Culture times of the matrix with growth factor range from 10 to 21 days. The concentration of growth factor used to treat the tissue matrix may range from 100 ng/ml to 10 µg/ml with a growth factor concentration for bFGF of 2.5 µg/ml being preferred.

When fibroblasts are used as the graft-repopulating cells the culture medium may include Dulbecco's Modified Eagle Medium (GIBCO) with 5–15% added serum. Autologous recipient serum is preferred but experience with implantation of allograft heart valves suggests that bovine serum may be utilized in the growth medium without adverse immunologic consequences to the implant recipient. Continual stimulation of the cells with serum and medium conditioned by the repopulating cells may provoke a more rapid cellular repopulation of the tissue matrix. The matrix, cells and growth factors may be incubated in a humidified atmosphere at 37° C. provided with a 95% air and 5% $CO_2$ mixture throughout the culture period.

The transplant tissue matrix is cultured for a time sufficient to produce a repopulated graft with interstitial histology similar to that of fresh tissue. Upon conclusion of the cellular repopulation process, the tissue will also preferably display metabolic parameters similar to those of fresh tissue.

Cellular Viability

An important aspect of this invention is that the repopulated transplant tissues are functioning and viable prior to implantation in addition to being immunologically acceptable to the implant recipient or substantially non-immunogenic. Various assays exist to measure cellular activity and application of these assays to the implant tissues of this process provide a method of monitoring and quantifying the viability of the cells which repopulate the implant tissue.

It is preferable that an assay be selected that measures a cellular activity which bears a relation to the intended function of the transplant tissue. For example, the production of collagen is important in maintaining a functioning heart valve. In heart valve leaflets 5 to 15% of the total protein produced is collagen. Of that at least 75% will be type I collagen. Therefore in assaying a repopulated heart valve, it is preferable to assay for total collagen produced by the repopulating cells as an accurate measure of cellular viability. Assaying for cellular activity by measuring collagen production are well known in the art. Examples of references discussing assays for cellular collagen production are Buckley, A. et al. 1980 *Collagen Metabolism., Methods of Enzymology*, 163:674–69, and Hayashi, T. and Nagai, Y. 1979. Separation of the α Chains of Type I and III Collagens by SDS-polyacrylamide Gel Electrophoresis, Journal of Biochemistry. 86:453–459, and are hereby incorporated by reference.

Other assays that can measure cell viability are envisioned for use in this invention. Total protein synthesis as measured by the incorporation of [$^3$H]proline is one such assay. Additional assays which may be useful in measuring cellular viability include assays for the metabolization of glucose and a variety of assays directed toward mitochondrial activity.

It is envisioned that any assay that quantifiably measures a cellular function indicative of viable cells may be used.

Differentiated Functions

Fibroblast cells are responsible for the production of most connective tissue components. They synthesize different collagen types, and the phenotype appears to be imposed by specific tissue environments; i.e., cultured fibroblasts synthesize collagen types according to their site of origin. Fibroblasts also produce various glycosaminoglycans and fibronectin and growth factors. It is the ability of dermal fibroblasts to synthesize types I, III, and V collagens in the proportion present in the matrix of the heart valve leaflet which makes them appropriate cells for repopulating the transplant tissue matrix and forming the hybrid graft described herein.

The cells which are used to repopulate the particular graft can be varied within wide limits, and different types of cells can be used in different circumstances, depending upon the function of the transplant, the nature of the tissue being replaced or augmented, the allergic sensitivity of the recipient in addition to other factors.

A preferred embodiment of the invention uses autologous cells in the process described herein. A tissue sample is taken from the recipient prior to transplant or implant surgery. The tissue is treated, in accordance with the methods described herein below, to produce fibroblasts or other cells which are then used to repopulate the allogeneic or xongeneic tissue matrix, in accordance with this process. By repopulating the previously prepared decellularized and treated transplant tissue matrix with cells derived from the resected tissue taken from the recipient, the likelihood of an adverse immune system response and ultimately graft rejection can be minimized or avoided.

The cell source can be selected to match the tissue to be transplanted. For example, if a blood vessel is to be transplanted, cells can be taken from a recipient's healthy blood vessel and used as the source of cells for graft repopulation. In this fashion, the healthy graft can be very closely matched to the recipient's diseased tissue.

This aspect of the invention is particularly useful when the transplant recipient is highly allergic, or if the tissue is highly immunogenic, such as with respect to transplantable blood vessels.

Alternatively, allogeneic cell lines which are not likely to cause an unacceptable immune response upon implant may be used to repopulate the tissue matrix. Cells with no more than a weak or tolerable allergic response may be used to repopulate the tissue matrix to provide a substantially non-immunogenic implant. These cells may be naturally weakly immunogenic or be designed by virtue of recombinant cell technology to be weakly immunogenic.

Method for Isolating Fibroblasts

The tissue used to provide the fibroblast cell link, for example skin (buttocks, thigh, or back) or heart valve leaflets, is recovered sterilely and provided to a processor in buffered nutrient medium. The tissue is cut into 1 mm$^3$ pieces using a sterile dissection technique. Groups of 10 pieces are then placed in 35 mm tissue culture dishes with a limiting amount of culture medium (DMEM plus 10% fetal bovine serum) sufficient to wet the tissue but not float the pieces. Incubate for one week at 37° C. in a humidified culture incubator in a 5% $CO_2$ atmosphere in air. After one week of incubation, each piece of tissue is surrounded by a dense outgrowth of fibroblasts. Epithelial cells may also be present but are lost during subsequent cell culturing. The fibroblasts are removed by standard trypsin digestion after rinsing the cells with a calcium and magnesium-free sterile buffered salt solution, and placed in larger cell culture vessels with fresh culture medium. The cell cultures can be expanded in this manner. The contents of one flask can be divided and placed into three larger vessels, and this process can be repeated about once a week. Cells recovered from these flasks are used as the source of repopulating cells. Cells obtained in this manner are preferable to commercially available cell lines, because most cell lines are phenotypically altered and are no longer responsive in a normal manner to growth regulators (such as bFGF). Additionally most commercially available cell lines do not produce natural amounts and proportions of important protein products (such as collagen).

A preferred embodiment of the invention encompasses a xenograft treated to remove native cells and soluble proteins, the conditions are chosen to be non-toxic to cells used to repopulate the xenograft and chosen to render the final xenograft tissue matrix biomechanically sound and intact. The depopulated xenograft tissue matrix is then treated with extracellular matrix glycoprotein factor and glycosaminoglycan. The xenograft is then treated with a growth factor and gtycosaminoglycan and incubated with exogenous cells that adhere to the graft. These exogenous cell migrate into the graft, proliferate within the graft, and express essential proteins and other factors critical to the function of the graft. The repopulated xenograft is rendered biologically functional by the repopulating cells and displays reduced or minimal immunogenicity as compared to either untreated xenograft or chemically-fixed xenograft. The reduced antigenicity is a consequence of the removal of xenoantigens or alloantigens during the initial depopulation of the tissue, and by the presence of repopulating cells which are not recognized as foreign by the recipient. These chimeric grafts should also display a reduced tendency for calcification because cell debris, which forms either as the result of cell death during procurement of tissue or during the decellularization of the tissue, is removed by the washing regimen. Because these chimeric grafts retain a lining layer of cells as a result of the above described procedure, the tendency of thrombi and microemboli to form should also be is reduced as compared to mechanical structures, structures made of purified biological molecules, and chemically-fixed bioprosthetic tissues.

EXAMPLES

Example 1. Depopulation of porcine aortic valve leaflets, aortic conduit, and associated myocardium according to hypotonic lysis/nuclease digestion procedure Pig hearts were obtained within two hours of slaughter, in order to limit the effects of uncontrolled cellular degradation on tissue structure, and returned to the processing facility at 4° C. in a sterile solution of DMEM. Aortic heart valves were excised under sterile conditions, incubated in antibiotic mixture for 16 hr at 37° C. in nutrient medium in 5% $CO_2$ atmosphere, and cryopreserved (cooling rate $\approx -1°$ C./min) in DMEM containing 10% DMSO and 10% fetal bovine serum. After storage at −179° C., the valves were thawed rapidly at 37° C. The leaflets, aortic conduit, and myocardium were cut from the valve and divided portions of each tissue type were either placed directly into 10% buffered formalin for later histologic analysis or were processed for depopulation. After washing in lactated Ringers—5% dextrose solution three times for 15 min each at room temperature, tissues were incubated in 18 MΩ water for 2 hr at room temperature followed by digestion in 10 µg/ml DNAase I and 1 µg/ml RNAase A in 10 Mm Tris-Cl, pH 7.6, containing 3 mM magnesium and 1 mM calcium salts at 37° C. for 120 min.

Figure 2A:
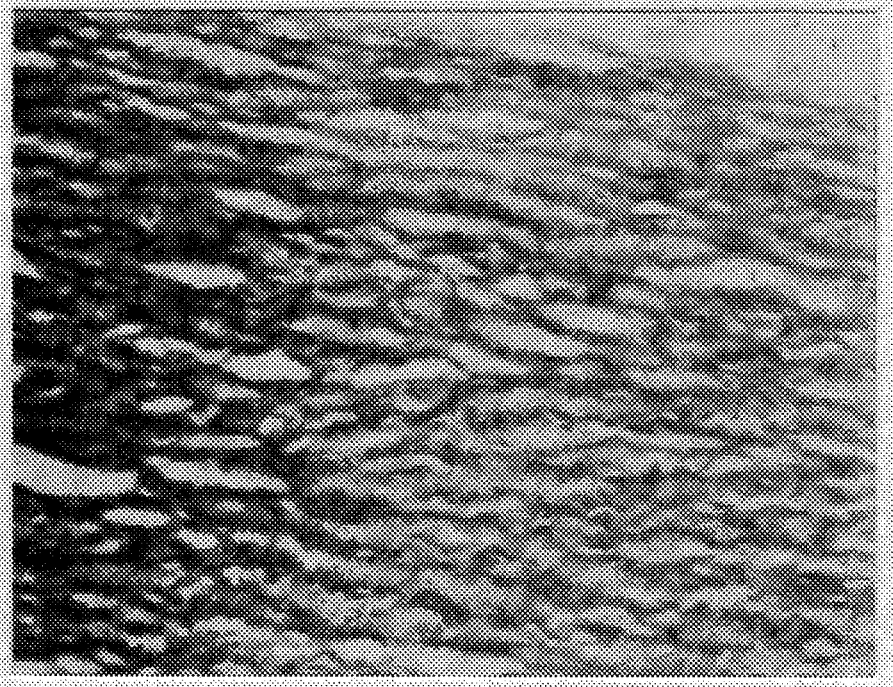
FIG. 2a. Photomicrograph showing pulmonary valve conduit after decellularization.
Figure 2B:
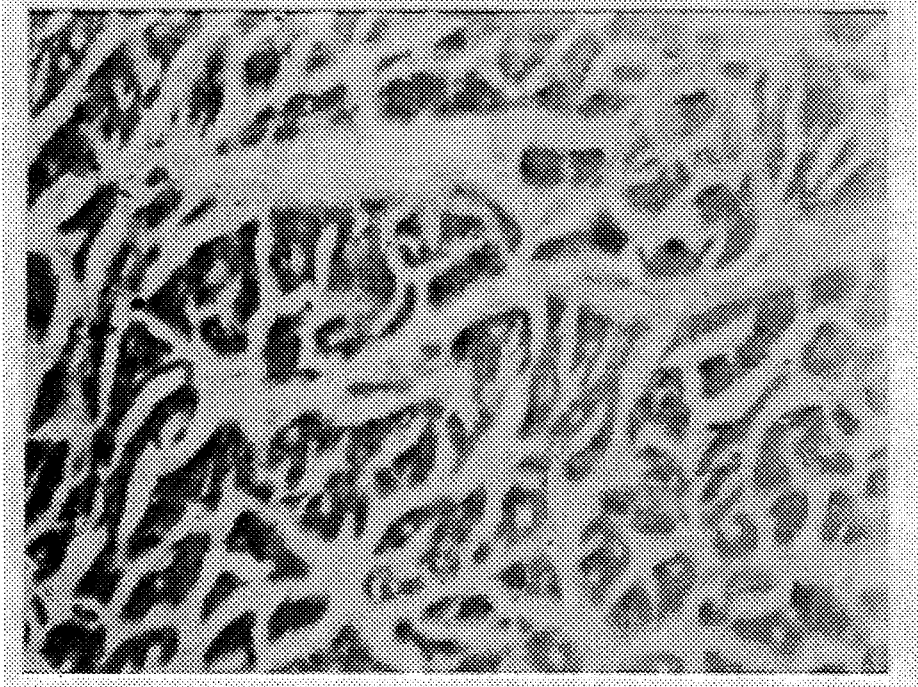
FIG. 2b. Photomicrograph showing myocardium after decellularization.

After lyric treatments, tissues were incubated for 8 days in DMEM—5% FBS. At this time, the treated tissues were fixed in formalin. All fixed tissues were mounted in paraffin, sectioned, and stained with hematoxylin and eosin to visualize cells. A representative micrograph in FIG. 1 shows the pattern of cellularity of a fresh aortic leaflet with an endothelial layer on both the fibrosa and ventricularis surfaces and fibroblasts throughout the full thickness of the tissue. FIGS. 2a and 2b show micrographs of pulmonary valve conduit and myocardium, respectively, after depopulation with essentially acellular appearance.

Figure 3A:
FIG. 3a. Photomicrograph of decellularized aortic leaflet.
Figure 3B:
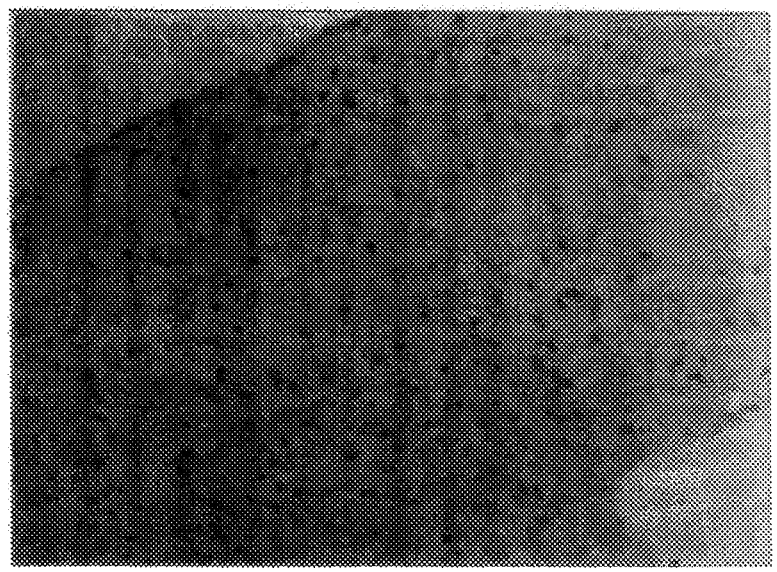
FIG. 3b. Photomicrograph of repopulated aortic leaflet.

Example 2. Repopulation of depopulated porcine aortic valve leaflets with bovine dermal fibroblasts Porcine aortic leaflets were recovered and depopulated as defined in Example 1. Leaflets were incubated in 5 ml $NaH_2PO_4$/glycerin/BSA buffer at 37° C. Human plasma fibronectin was added to the buffer to a concentration of 10 µg/ml along with 1 µg/ml heparin for 16 hr followed with addition of human recombinant bFGF to a concentration of 2.5 µg/ml along with 0.83 µg/ml heparin for an additional 6 hr. After this incubation, bovine dermal fibroblasts, previously isolated by standard explant culture techniques, were added to the heart valve leaflets at $2\times10^4$ cell/ml. The leaflets and cells were incubated for 11 days. Following incubation, valve sections were placed in formal for histologic analysis. FIG. 3a is a representative micrograph of a decellularized aortic leaflet. FIG. 3b is a representative micrograph of a decellularized aortic leaflet treated with both fibronectin and bFGF showing repopulation with exogenous fibroblasts.

Example 3. Biochemical activity of fibroblasts in repopulated as compared to fresh and depopulated tissues Porcine aortic heart valve leaflets were depopulated as in Example 1 and repopulated with two different isolates of sheep dermal fibroblasts according to the technique in Example 2. After 10 days of repopulation, leaflets were moved to fresh vessels and incubated for 48 hr in 1.0 µCi/ml [$^3$H]proline in DMEM containing gentamycin and 50 µg/ml ascorbic acid, 50 µg/ml β-aminopropionitrile. Total proteins synthesized were determined by 10% trichloroacetic acid precipitated radioactivity recovered from medium and tissue extracts made 10 mM in N-ethylmaleimide, 25 mM in EDTA, and 10 mM in phenylmethylsulfonyl fluoride to prevent proteolysis; precipitated protein was further analyzed by digestion with Clostridial collagenase free of non-specific protease activity to define the collagen content. As shown in FIGS. 4a, 4b, 4c, and 4d protein synthetic activity of depopulated tissue was nil. Following repopulation, significant protein synthesis was detected by [$^3$H]proline incorporation which was synthesized at the same rate as was determined in fresh porcine tissue; collagen represented 3.6% of the total protein synthesis, and most of this was secreted into the medium. These results indicate that porcine leaflets rendered treated by the depopulation procedures described in the preferred embodiment of the invention display no protein synthetic capacity in general and no collagen synthesis in particular. The successful application of repopulation procedures is indicated by the ability to impart the cellular function of protein synthesis to the depopulated leaflet by the provision of exogenous fibroblasts during the repopulation procedure.

Figure 5A:
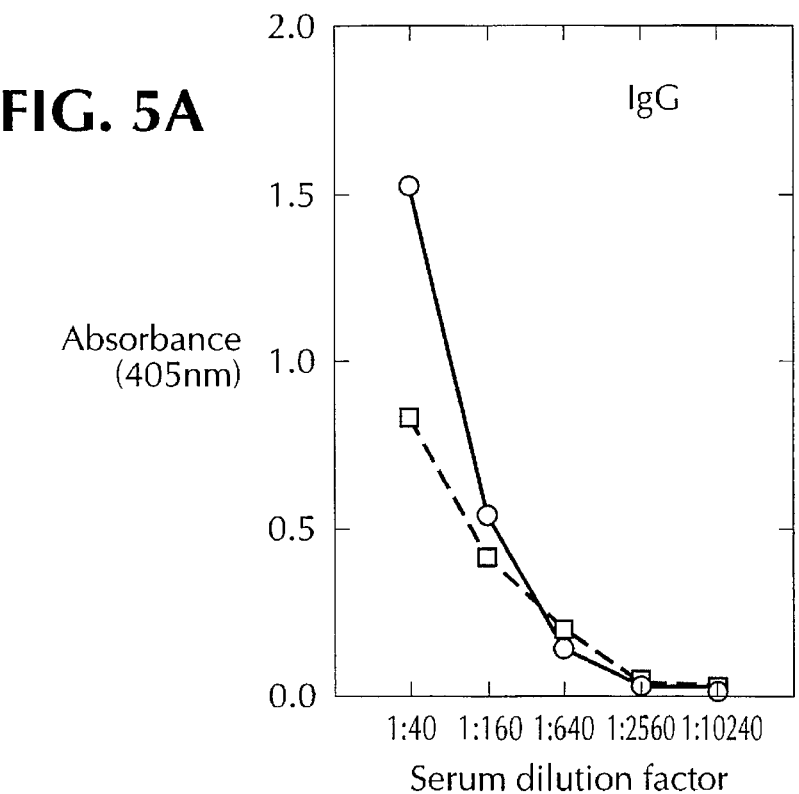
FIG. 5a. Reactivity of Rabbit IgG Antisera Raised to Extracts of Cryopreserved or Depopulated Porcine Heart Valve Leaflets—Antibody Capture.
Figure 5B:
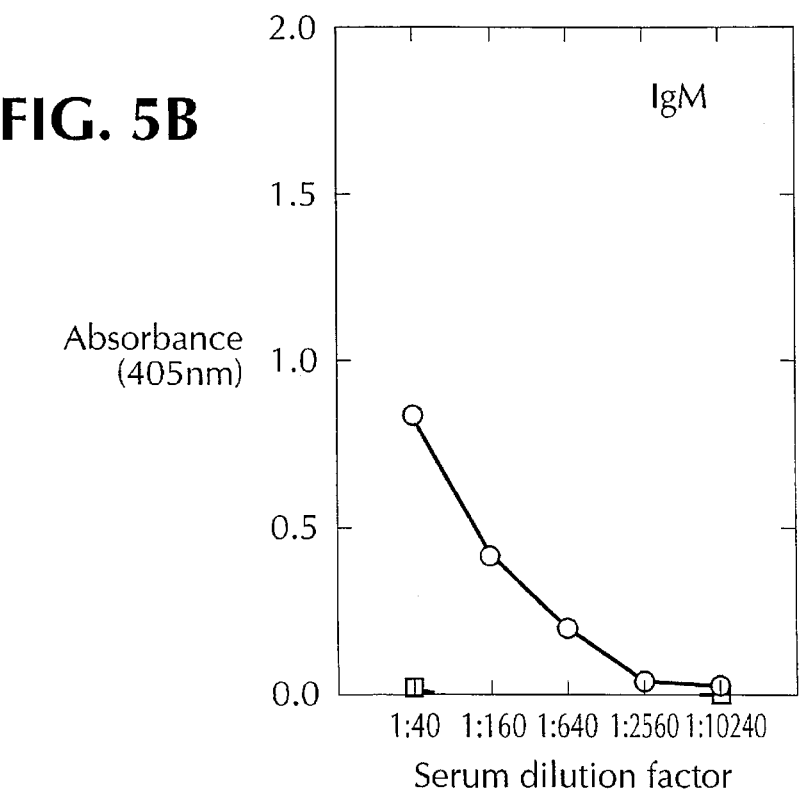
FIG. 5b. Reactivity of Rabbit IgM Antisera Raised to Extracts of Cryopreserved or Depopulated Porcine Heart Valve Leaflets—Antibody Capture.

Example 4. Demonstration of reduced humoral immune response to depopulated porcine leaflet extracts injected in rabbits Removal of cells and soluble proteins was achieved by procedures described in Example 1. The immunological consequences of depopulating leaflets were investigated by comparison with cryopreserved viable leaflets. The results of humoral immune response studies are presented in FIGS. 5a and 5b. The humoral immune response was assessed using an antibody capture technique in which antigen extracts in 0.1M NaCl of unmodified cryopreserved leaflets were used to screen sera from rabbits immunized with NaCl extracts of either modified cell depopulated leaflets or control leaflets. Emulsions of such extracts were made in 50% (v/v) Freund's complete adjuvant; 0.1 ml portions of these emulsions were placed at ten intradermal sites along the backs of separate New Zealand white male rabbits. After two weeks, the animals were rechallenged with additional extracts of cryopreserved or depopulated leaflets emulsified in Freund's incomplete adjuvant. After 1.5 months, the animals were bled. Immune sera were prepared and were screened for both IgG and IgM antibodies using goat anti-rabbit igG and goat anti-rabbit IgM antisera conjugated to alkaline phosphatase. In FIGS. 5a and 5b, the serum from depopulated tissue recipients demonstrated ~50% of the IgG response and <5% of the igM response observed in rabbits immunized with cryopreserved leaflet extracts. These findings indicate attenuation of the humoral immune response to tissue depopulated by the techniques described in the preferred embodiment of the invention.

Figure 6A:
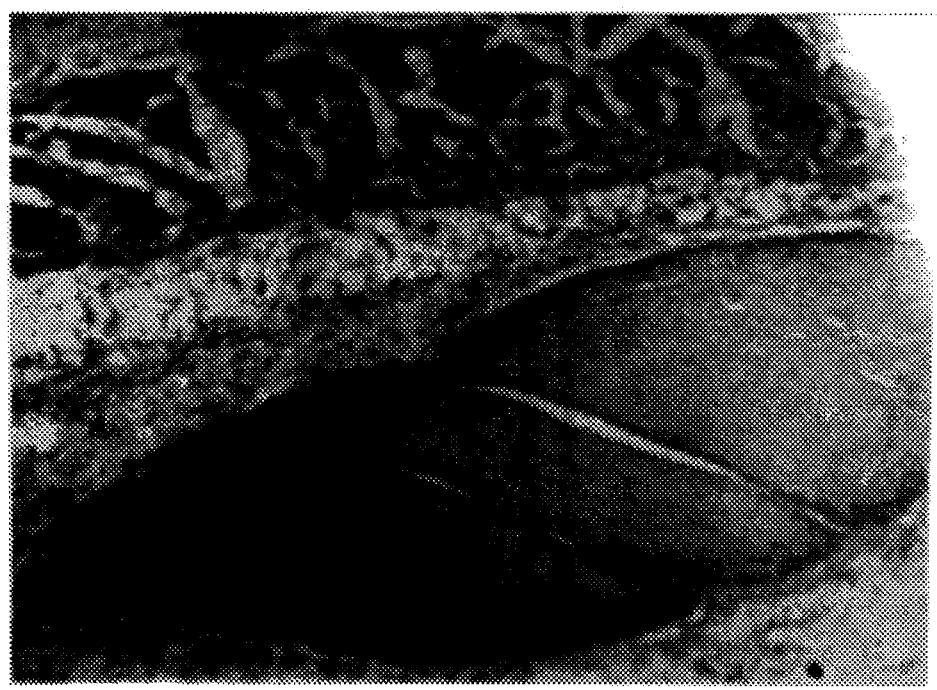
FIG. 6a. Photomicrograph showing the minimal cellular response triggered by decellularized porcine heart valve leaflets after implantation.
Figure 6B:
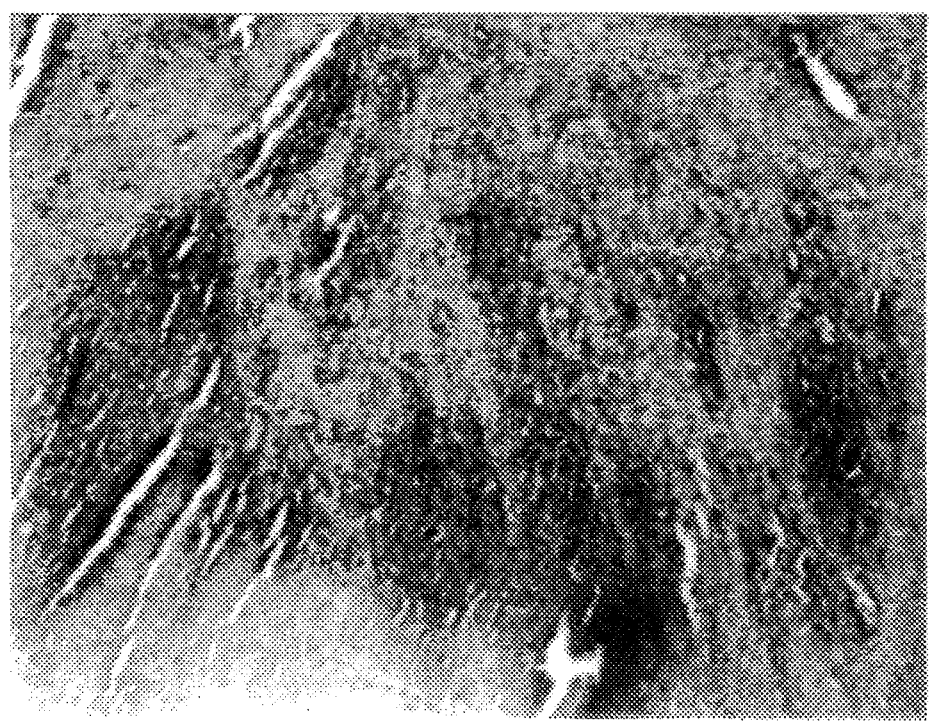
FIG. 6b. Photomicrograph showing cellular response triggered by cryopreserved porcine aortic valve leaflet after implantation.

Example 5. Demonstration of reduced cellular immune and inflammatory responses to depopulated porcine leaflets implanted in rabbits Removal of cells and soluble proteins was achieved by procedures described in Example 1. Divided pieces of depopulated (acellular) and cryopreserved (cellular) porcine aortic valve leaflets were inserted into pouches formed in the dorsal subcubitae of New Zealand white male rabbits. The pouches were closed and after two weeks the implants and surrounding tissues (skin to muscle) were recovered surgically and fixed in formalin for histopathologic analysis after staining paraffin embedded sections with hematoxylin and eosin. FIG. 6 shows that depopulated leaflets engendered minimal cellular responses compared with cryopreserved controls. The cryopreserved tissue which contains both an endothelial cell layer as well as fibroblasts stimulated significant immune and inflammatory cell response with large numbers of heterophils and lymphocytes and plasma cells in the implant area as well as within the implants themselves. In depopulated tissue implants, both inflammatory and immune cells were fewer in number and more limited in distribution.

Figure 7A:
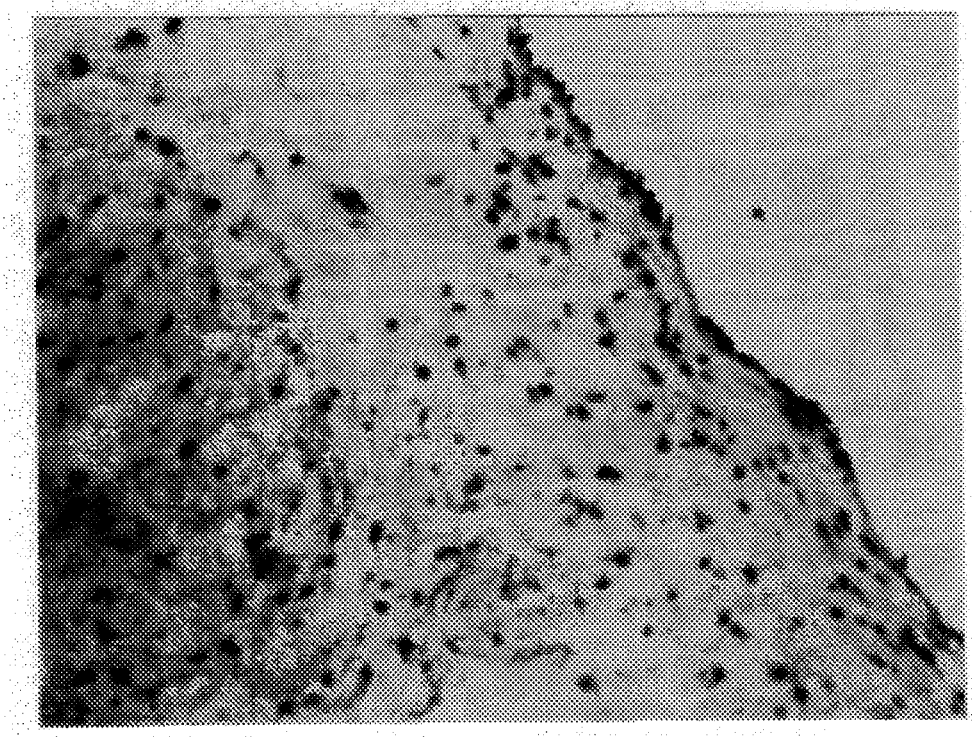
FIG. 7a. Photomicrograph of fresh porcine aortic valve leaflet assayed for pig cell associated antigen.
Figure 7B:
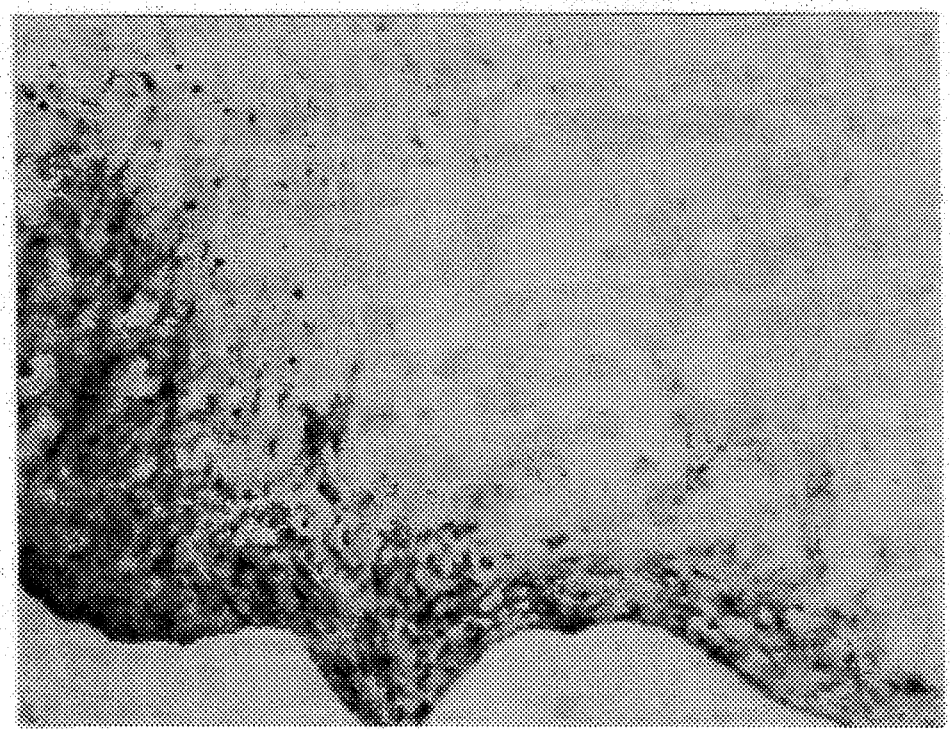
FIG. 7b. Photomicrograph of decellularized porcine aortic valve leaflet assayed for pig cell associated antigen.

Example 6. Demonstration of removal of antigens responsible for hyperacute rejection of porcine tissues in a human recipient Removal of cells and soluble proteins from porcine aortic heart valve leaflets and aortic conduit was achieved by procedures described in Example 1. Divided pieces of these tissues and their counterparts from fresh and cryopreserved porcine aortic heart valves were fresh-frozen in liquid nitrogen in cryosection mounting medium, cut into 8–10 μm sections, mounted on charge-modified glass slides. After fixation in 4° C. acetone, the tissues were probed with a biotin-conjugated Bandeiraea simplicifolia lectin-I which binds to specific galactose-$\alpha$1,3-galactose modified proteins found on the membranes of porcine cells. These modified proteins are the sites of binding of preformed natural anti-porcine antibodies that initiate hyperacute rejection responses of porcine tissues in primates (including man). Proteins binding this lectin were detected by then reacting the sections with biotin-conjugated horseradish peroxidase-avidin mixture, hydrogen peroxide, and 3,3'-diaminobenzidine. Presence of porcine antigens is detected by color development. In FIG. 7a, microscopic analysis of sections demonstrates cell associated antigen in cryopreserved aortic leaflet. FIG. 7b demonstrates markedly diminished antigen binding after decellularization of the aortic leaflet. This study shows that the depopulation procedure as presented in the preferred embodiment of the invention reduces critical antigens likely to cause rejection of a porcine graft by a human recipient.

Figure 8A:
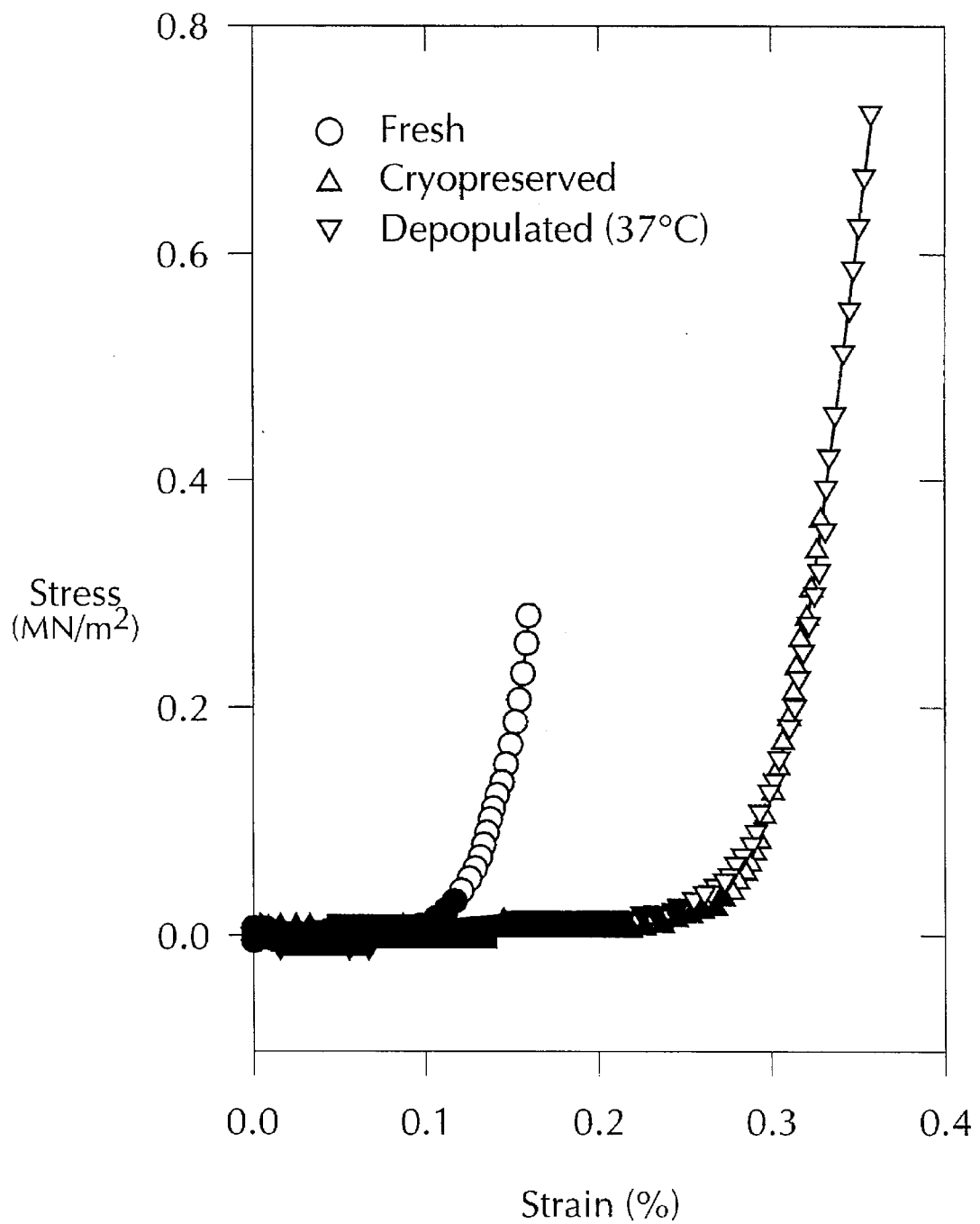
FIG. 8a. Stress-Strain Relations of Porcine Aortic Valve Leaflets.
Figure 8B:
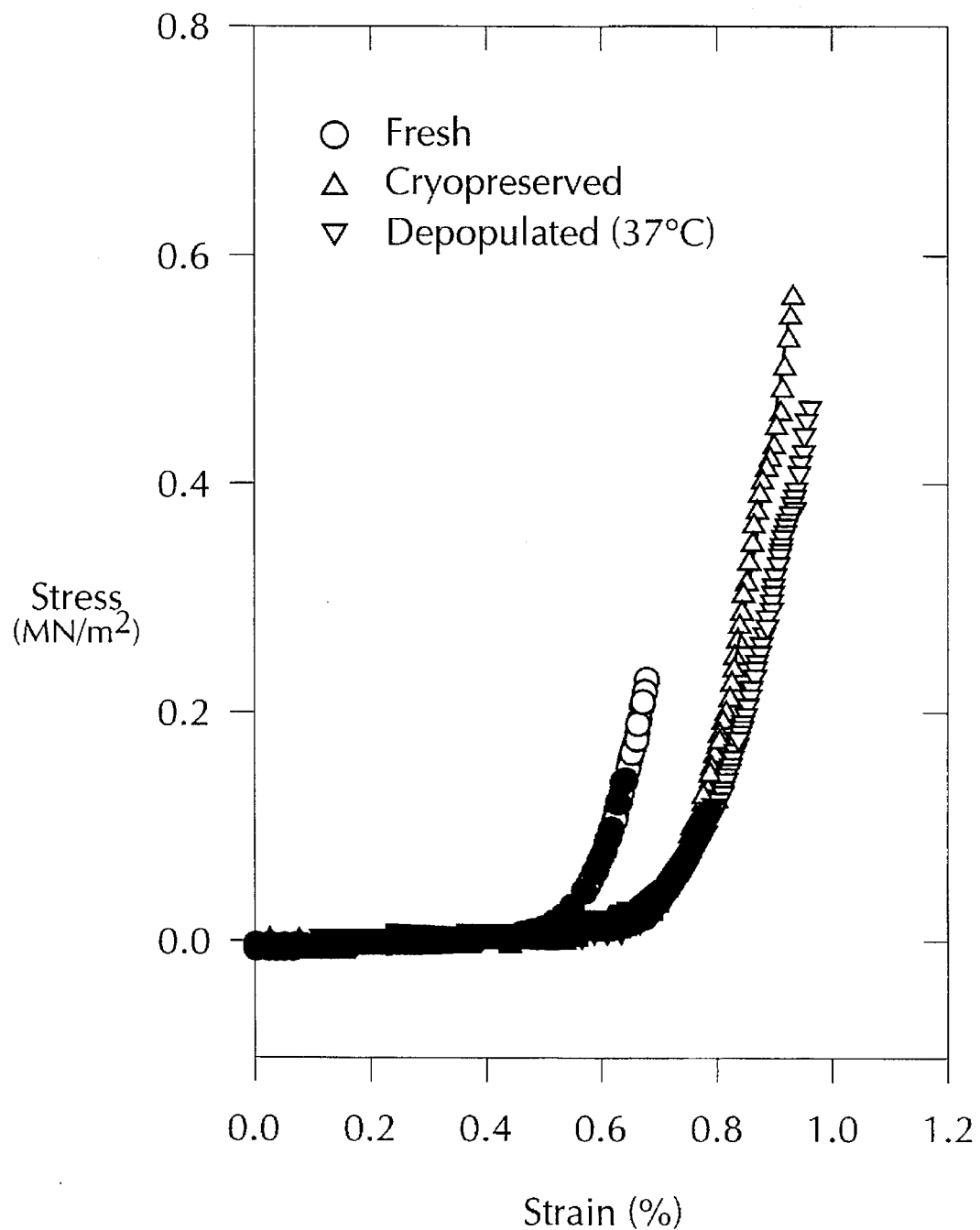
FIG. 8b. Stress-Strain relations of Porcine Aortic Valve Leaflets.
Figure 9A:
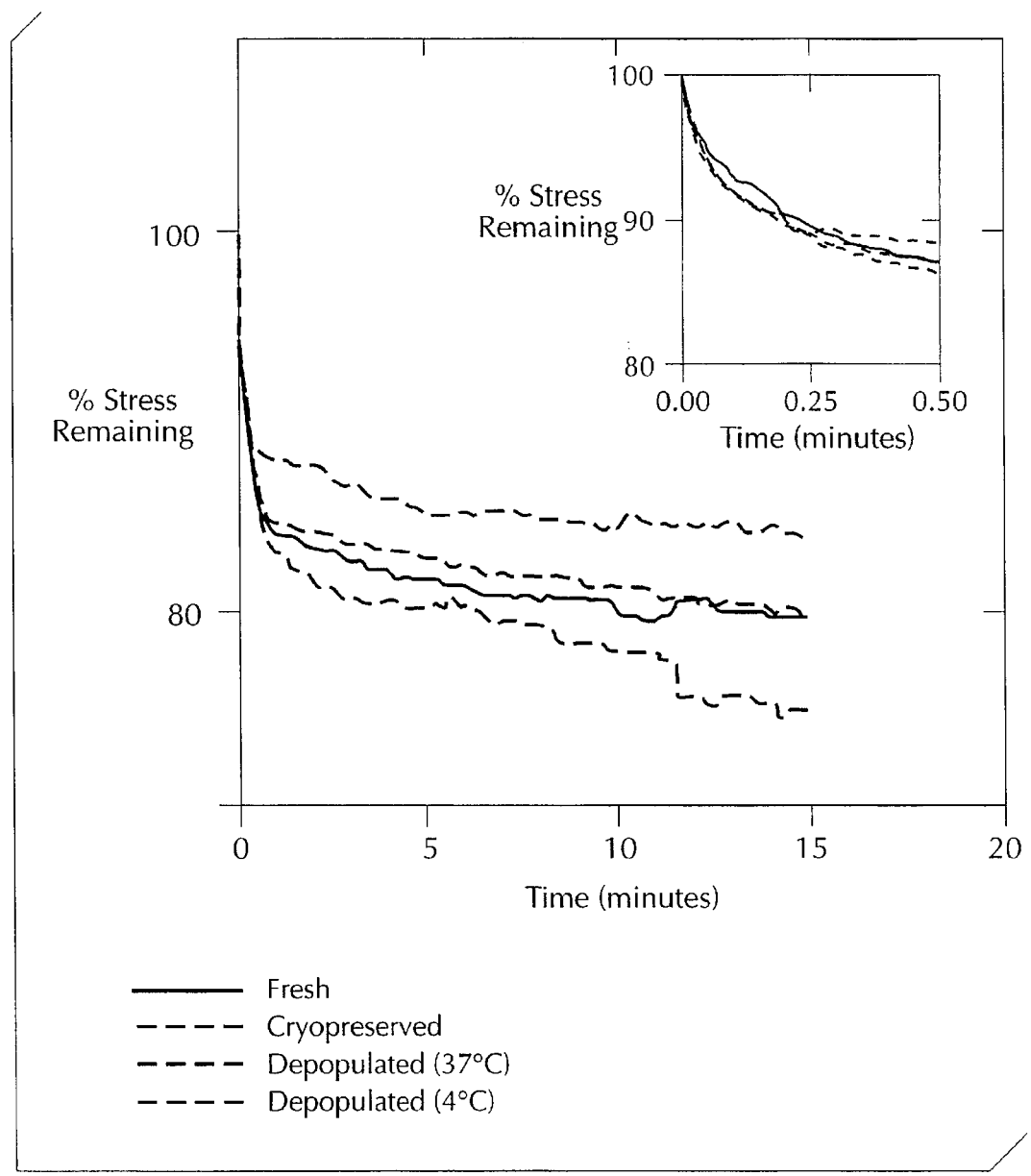
FIG. 9a. Stress Relaxation Curves of Porcine Aortic Leaflets After Preconditioning.
Figure 9B:
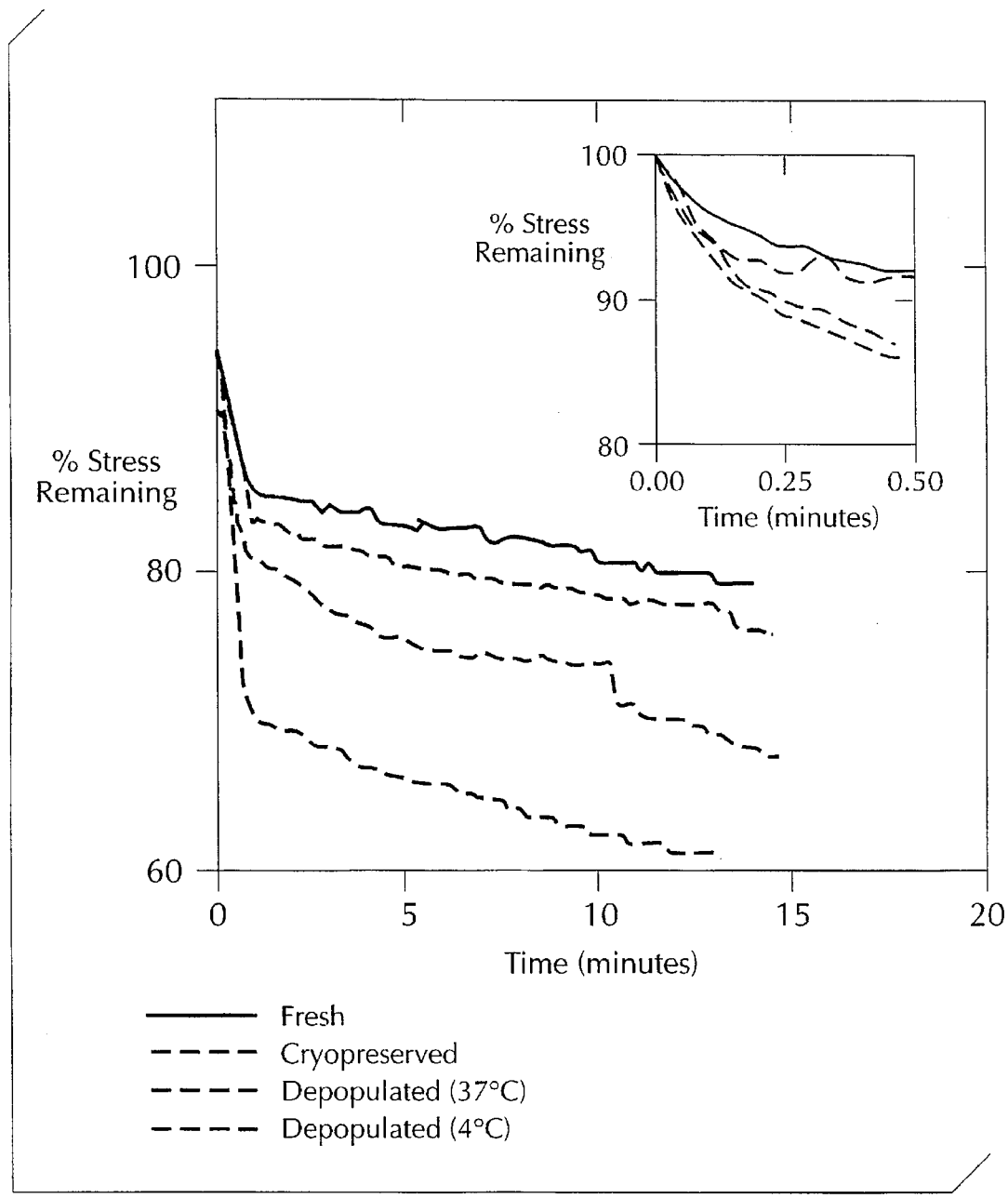
FIG. 9b. Stress Relaxation Curves of Porcine Aortic Leaflets After Preconditioning.

Example 7. Biomechanical properties of depopulated porcine aortic heart valve leaflets stress-strain analyses Porcine aortic heart valves, freshly obtained, were sterilized with antibiotic mixture and cryopreserved under conditions that maintain cellular viability. For depopulation, aortic valves were thawed rapidly at 37° C., then treated with low hypotonicity solution, nucleases, and balanced salt solution for 10 days. For biomechanical testing, leaflets were cut into circumferential or radial strips, mounted onto an Instron Model 1011 Materials Tester under calibrated clamping pressure. Tissue was bathed in 37° C. or 4° C. Hanks balanced salt solution during testing. After determination of gauge length and 20 preconditioning cycles (100 g load for circumferential strips and 180 g for radial strips), each specimen was tested as follows:

1) A single load versus elongation test, results of which are shown in FIGS. 8a and 8b. Radial strips were more extensible than circumferential under all conditions. Tissue modulus was unaffected by any treatment, but depopulated radial strips were significantly more extensible than fresh tissue (113±11.8 vs. 85.9±8.6 mm/mm);

2) A stress relaxation test, results of which are shown in FIGS. 9a and 9b. For circumferential and radial strips approximately 10% of the original stress was dissipated in the first 10 sec. Overall, the rate of loss of stress appeared greater in radial strips in general and was fastest in cryopreserved radial strips. At the termination of the test, stress remaining in 37° C. depopulated circumferential strips was significantly greater than in fresh tissue; there were no significant differences in the radial strips; and 3) A tensile failure test, results of which are shown in FIGS. 10a and 10b. For each condition, circumferential strips were stronger, stiffer, and tougher than radial strips. Cryopreservation and depopulation did not affect these parameters measured in the circumferential direction. Radial strips cut from tissue depopulated at either temperature did show greater toughness as compared to fresh.

The description contained herein contains the preferred embodiments of the invention. However, numerous alternative embodiments are contemplated as falling within the scope of the invention. By teaching and by example, the important features of the invention are demonstrated: 1) removal of xenogeneic cells and cell membranes from a tissue potentially useful as an implantable or transplantable graft in humans (shown by histologic and biochemical analyses); 2) under the influence of extracellular matrix glycoprotein, glycosaminoglycan, and growth factor, the acellular tissue can be repopulated with exogenous cells, potentially derived from the recipient of the grafts; 3) maintenance of biomechanical properties similar to those of cryopreserved tissues which are themselves utilized as stable graft materials; and 4) as a result of the depopulation procedure, the propensity of depopulated tissue to stimulate an inflammatory and cellular and humoral immune response in the recipient is reduced.

What is claimed is:

1. A process for generating a substantially non-immunogenic tissue matrix suitable for subsequent processing into an implant tissue comprising:
   A. eliminating native cells by treating a tissue with components selected from the group consisting enzymes and nucleases effective to inhibit subsequent native cell growth in the treated tissue and effective to limit generation of new immunological sites in the tissue thus producing a tissue matrix;
   B. treating the tissue matrix with cellular adhesion factor to promote subsequent attachment of cultured allogeneic or autologous cells to the surfaces of the tissue matrix; and
   C. repopulating the tissue matrix throughout the matrix with cultured allogeneic or autologous cells.

2. The process of claim 1 wherein, during step A, the tissue is treated with a low ionic strength solution of nucleases effective to decellularize the tissue and provide a tissue matrix of limited immunogenicity.

3. The process of claim 2 wherein the low ionic strength solution of nucleases includes at least one member, selected from the group consisting of RNAase A, DNAase I, EcoR I and Hind III.

4. The process of claim 2 wherein the nucleases employed are ribonuclease A and deoxyribonuclease I.

5. The process of claim 1 further comprising cryopreserving the tissue matrix after step A and prior to further processing.

6. The process of claim 2 further comprising cyropreserving the tissue matrix after step A and prior to further processing.

7. The process of claim 5 further comprising sterilizing the tissue or tissue matrix or both.

8. The process of claim 1 wherein the process further comprises obtaining natural mammalian tissue, cryopreserving the tissue, removing the tissue from cryopreservation and then treating the tissue in accordance with claim 1.

9. The process of claim 8 wherein the tissue is of porcine heart valve origin.

10. The process of claim 9 wherein the heart valve is a pulmonary or an aortic heart valve.

11. The process of claim 1 wherein step A further comprises treatment with a hypotonic aqueous solution.

12. The process of claim 11 herein said hypotonic aqueous solution is a buffered aqueous solution effective to cause cell lysis.

13. The process of claim 12 wherein the tissue is porcine heart valve tissue.

14. The process of claim 13 wherein the heart valve is a pulmonary or an aortic heart valve.

15. The process of claim 14 further comprising the step of cryopreserving the porcine heart valve tissue matrix produced by step A.

* * * * *